US005879677A

United States Patent [19]

del Zoppo

[11] Patent Number: 5,879,677

[45] Date of Patent: Mar. 9, 1999

[54] METHOD FOR INHIBITION OF CEREBRAL TISSUE FACTOR MEDIATED REPERFUSION DAMAGE

[75] Inventor: Gregory J. del Zoppo, La Jolla, Calif.

[73] Assignee: The Scripps Research Institute, La Jolla, Calif.

[21] Appl. No.: 372,887

[22] Filed: Jan. 13, 1995

Related U.S. Application Data

[63] Continuation of Ser. No. 987,637, Dec. 9, 1992, abandoned.

[51] Int. Cl.[6] .......... A61K 39/395

[52] U.S. Cl. .......... 424/145.1; 424/139.1; 424/141.1

[58] Field of Search .......... 424/139.1, 141.1, 424/145.1

[56] References Cited

U.S. PATENT DOCUMENTS

| | | |
|---|---|---|
| 4,797,277 | 1/1989 | Arfors . |
| 5,110,730 | 5/1992 | Edgington . |
| 5,223,427 | 6/1993 | Edington et al. . |
| 5,437,864 | 8/1995 | Edington et al. . |

FOREIGN PATENT DOCUMENTS

| | | |
|---|---|---|
| 8807543 | 10/1988 | WIPO . |
| 8912463 | 12/1989 | WIPO . |

OTHER PUBLICATIONS

Goldstein et al. (1986) Scientific American 255: 74–83.
Ragni, M. etal, Circulation, 93(10):1913–1918, 1996.
Creasey etal (1993) J. Clin.Invest. 91:2850–2860.
Del Zoppo etal (1986) Stroke 17(6):1254–1265.
Cete etal (1993) J. Clin. Invest. 92:1207–1212.
Morrissey etal (1988) Thrombosis Research 50:481–493.
Morrissey etal (1988) Thrombosis Research 52:247–261.
Ruf etal (1991) Thrombosis and Haemostasis vol. 66(5):529–533.
Carson etal. (1987) Blood 70(2):490–493.
Carpenter (1978) "CoreText of Necuoanatomy", Williams and Wilkna, Baltimore, p. 323.
Spicer etal (1987) Proc.Nat'l.Acad.Sci. 84:5148–5152.
Morrissey etal (1987) Cell 50:129–135.
Vedder etal (1990) Proc.Nat'l Acad Sci. 87:2643–2646.
Drake etal (1989) Amer. J. Pathol. 134(5):1087–1097.
del Zoppo etal (1986) Stroke 17(6):1254–1255 (abstract only).
del Zoppo etal (1991) Throm.Haemost. 65(6):682, (Abstr.#113).
Davie etal (1991) Biochemistry 30(43):10363–10370.
Broze etal (1985) J. Biol. Chem. 260(20):10917–10920.
Thomas etal (1993) Stroke 24: 847–854.
Harlow etal (1988) "Antibodies & A Laboratory Manual," Cold Spring Harbor Press, Cold Spring Harbor, NY, pp. 72–77, 92–97, 128–135 & 141–157.
Ruf etal (1992) J. Biol. Chem. 267(31): 22206–22210.
Thorpe (1993) Trends in Biotelinol 11:40–42.
Fitzer–Schiller (1993) The Washington Post, p. D3 (19 Jan.).
del Zoppo, et al. Polymorphonuclear Leukocytes Occlude Capillaries . . . Stroke, vol. 22, No. 10, Oct. 1991, pp. 1276–1283.
Mori, M.D., et al.; Inhibition of Polymorphonuclear Leukocyte . . . Stroke; vol. 23, No. 4, May 1992, pp. 712–718.
del Zoppo, et al., Tissue Factor Localization in Non–Human Primate . . . Thrombosis and Haemostasis, 1992, pp. 642–647, vol. 68.

*Primary Examiner*—Paula K. Hutzell
*Assistant Examiner*—Patricia A. Duffy
*Attorney, Agent, or Firm*—Fish & Richardson, P.C.

[57] ABSTRACT

Tissue factor mediated reperfusion damage is inhibited in a subject by administration of tissue factor-specific monoclonal antibodies of tissue factor peptides which prevent tissue factor from binding to Factor VII/VIIa in order to modulate coagulation.

5 Claims, 9 Drawing Sheets

```
                                    M  E  T  P  A  W  P  R  V  P  R  P  E  T  A  V  A  R  T
CGTTCCGCTCGATCTCGCCGCCAACTGGTAGACATGGAGACCCCTGCCTGGCCCCGGGTCCCGCGCCCCGAGACCGCCGTCGCTCGGACG
        10        20        30        40        50        60        70        80        90

 L  L  L  G  W  V  F  A  Q  V  A  G  A  S  G  T  T  N  T  V  A  A  Y  N  L  T  W  K  S  T
CTCCTGCTCGGCTGGGTCTTCGCCCAGGTGGCCGGCGCTTCAGGCACTACAAATACTGTGGCAGCATATAATTTAACTTGGAAATCAACT
       100       110       120       130       140       150       160       170       180

 N  F  K  T  I  L  E  W  E  P  K  P  V  N  Q  V  Y  T  V  Q  I  S  T  K  S  G  D  W  K  S
AATTTCAAGACAATTTTGGAGTGGGAACCCAAACCCGTCAATCAAGTCTACACTGTTCAAATAAGCACTAAGTCAGGAGATTGGAAAAGC
       190       200       210       220       230       240       250       260       270

 K  C  F  Y  T  T  D  T  E  C  D  L  T  D  E  I  V  K  D  V  K  Q  T  Y  L  A  R  V  F  S
AAATGCTTTTACACAACAGACACAGAGTGTGACCTCACCGACGAGATTGTGAAGGATGTGAAGCAGACGTACTTGGCACGGGTCTTCTCC
       280       290       300       310       320       330       340       350       360

 Y  P  A  G  N  V  E  S  T  G  S  A  G  E  P  L  Y  E  N  S  P  E  F  T  P  Y  L  E  T  N
TACCCGGCAGGGAATGTGGAGAGCACCGGTTCTGCTGGGGAGCCTCTGTATGAGAACTCCCCAGAGTTCACACCTTACCTGGAGACAAAC
       370       380       390       400       410       420       430       440       450

 L  G  Q  P  T  I  Q  S  F  E  Q  V  G  T  K  V  N  V  T  V  E  D  E  R  T  L  V  R  R  N
CTCGGACAGCCAACAATTCAGAGTTTTGAACAGGTGGGAACAAAAGTGAATGTGACCGTAGAAGATGAACGGACTTTAGTCAGAAGGAAC
       460       470       480       490       500       510       520       530       540
```

FIG. 1a

```
N  T  F  L  S  L  R  D  V  F  G  K  D  L  I  Y  T  L  Y  Y  W  K  S  S  S  S  G  K  K  T
AACACTTTCCTAAGCCTCCGGGATGTTTTTGGCAAGGACTTAATTTATACACTTTATTATTGGAAATCTTCAAGTTCAGGAAAGAAAACA
        550       560       570       580       590       600       610       620       630

A  K  T  N  T  N  E  F  L  I  D  V  D  K  G  E  N  Y  C  F  S  V  Q  A  V  I  P  S  R  T
GCCAAAACAAACACTAATGAGTTTTTGATTGATGTGGATAAAGGAGAAAACTACTGTTTCAGTGTTCAAGCAGTGATTCCCTCCCGAACA
        640       650       660       670       680       690       700       710       720

V  N  R  K  S  T  D  S  P  V  E  C  M  G  Q  E  K  G  E  F  R  E  I  F  Y  I  I  G  A  V
GTTAACCGGAAGAGTACAGACAGCCCGGTAGAGTGTATGGGCCAGGAGAAAGGGGAATTCAGAGAAATATTCTACATCATTGGAGCTGTG
        730       740       750       760       770       780       790       800       810

V  F  V  V  I  I  L  V  I  I  L  A  I  S  L  H  K  C  R  K  A  G  V  G  Q  S  W  K  E  N
GTATTTGTGGTCATCATCCTTGTCATCATCCTGGCTATATCTCTACACAAGTGTAGAAAGGCAGGAGTGGGGCAGAGCTGGAAGGAGAAC
        820       830       840       850       860       870       880       890       900

S  P  L  N  V  S  *
TCCCCACTGAATGTTTCATAAAGGAAGCACTGTTGGAGCTACTGCAAATGCTATATTGCACTGTGACCGAGAACTTTTAAGAGTGCCCTA
        910       920       930       940       950       960       970       980       990

GGACAGAACCTGTGCCAGAAAGGAAAGTAAAGGAACAGTGCCGAGTGGAAGTCCAGAGGCAAGAAGGAACATGGCAGGATGCAGGTACAGG
       1000      1010      1020      1030      1040      1050      1060      1070      1080

AGGGTGCATAGCCTGGCCTGAGTGCTGTGTTCTGGAAAGGAGTGG
       1090      1100      1110      1120
```

FIG. 1b

METHOD FOR INHIBITION OF CEREBRAL TISSUE FACTOR MEDIATED REPERFUSION DAMAGE

This is a continuation of application Ser. No. 07/987,637 filed on Dec. 9, 1992, now abandoned.

This invention was made with Government support under Grant No. NS 26945 awarded by the National Institutes of Health. The Government has certain rights in this invention.

BACKGROUND OF THE INVENTION

1. Field of the Invention

This invention relates to the formation of blood clots and specifically to the inhibition of blood clot formation and tissue damage following reperfusion.

2. Description of Related Art

The clotting of blood involves a cascade of enzymes, cofactors, and a group of cellular and plasma proteins known as coagulation factors. Initiation of this cascade occurs when the cellular receptor, known as tissue factor (TF), binds coagulation factor VII or its derivative, factor VIIa, to form a catalytically active complex. Factors X and IX. are activated by the TF-VIIa complex, thereby catalyzing thrombin generation and fibrin formation. TF is a membrane-bound glycoprotein that is not normally found soluble in the circulation or accessible to plasma proteins including factor VII/VIIa and the other coagulation factors.

TF is the principal procoagulant in the human brain. TF has been localized to the parenchyma of the adult human cerebral cortex, where it has a diffuse distribution (Drake, et al., *Am.J.Pathol.,* 134:1087, 1989). The appearance of TF on stimulated endothelial cells and cells of the monocyte/macrophage lineage in vitro suggests a vascular association of the procoagulant, which is supported by the perivascular localization of TF antigen in non-neural tissues. Electron microscopy has demonstrated fibrin in microvessels associated with degranulated platelets/polymorphonuclear leukocytes, but not in capillaries following middle cerebral artery (MCA) occlusion/reperfusion (del Zoppo, et al., *Stroke,* 22:1276, 1991). The exposure of TF to plasma during vascular ischemia may contribute to intravascular coagulation defects.

TF, which is found predominantly in cerebral tissues and on perivascular cells, may be a contributor to the development of microvascular occlusions. In the brain, TF has a prominent perivascular distribution around non-capillary cerebral microvessels, especially in gray matter. Tissue factor is constitutively expressed on the surface of some extravascular cells in vitro including fibroblasts and certain epithelial cells that are separated from the circulating plasma proteins by basement membrane barriers. The presence of TF on these cells results in clot formation upon contact with blood and tissue damage thereby occurs.

Incomplete perfusion of the microvasculature following transient focal or global cerebral ischemia and reperfusion (I/R) constitutes the "no-reflow" phenomenon. Polymorphonuclear leukocytes and platelets, in addition to other endothelium and subendothelium-related mechanisms, have been implicated in the formation of these perfusion defects. Little is known concerning the role of fibrin formation, or other consequences of local thrombin generation, in causing microvascular obstruction following focal cerebral ischemia/reperfusion. In addition to cellular contributions to the microvascular perfusion defect following focal cerebral I/R, coagulation system activation may play a role. A role for the coagulation system in tissue damage has been suggested by studies showing the ability of the combination of heparin/ticlopidine to significantly reduce post-I/R microvascular occlusion formation and platelet deposition in a non-human primate model (del Zoppo, et al. *Stroke* 17(6):1254, 1986). Thus, methods which can inhibit reperfusion tissue damage would be of significant clinical value. The present invention provides such a method.

SUMMARY OF THE INVENTION

The present invention arose out of the unexpected discovery that tissue factor (TF)-initiated coagulation plays a role in the tissue damage following vascular reperfusion. The inventor has provided data showing, for the first time, that TF-mediated fibrin formation contributes to the "no-reflow" phenomenon in focal cerebral ischemia. Thus, the invention provides a method of inhibiting TF-mediated reperfusion tissue damage in a subject, comprising administering to the subject a therapeutically effective amount of a tissue factor inhibitor. The TF inhibitor may be any reagent which blocks the formation of a TF:factor VII/VIIa complex, thereby inhibiting the initiation of the coagulation cascade. For example, the TF inhibitor can be a monoclonal antibody which binds TF so that TF can no longer bind factor VII/VIIa. Alternatively, the TF inhibitor can be a polypeptide binding site analog which binds factor VII/VIIa so that TF can no longer bind factor VII/VIIa thereby blocking formation of the active complex which initiates coagulation. The method of the invention can be envisioned to prevent TF-mediated reperfusion tissue damage in any tissue in a subject and most preferably tissue in the brain and in the heart.

BRIEF DESCRIPTION OF THE DRAWINGS

FIGS. 1*a* and 1*b* are the nucleotide sequence (SEQ ID NO: 19) and corresponding amino acid sequence (SEQ ID NO: 20) for human tissue factor (shown as 5' to 3' for the nucleotide sequence and from N to C terminus, beginning with methionine as shown). The structural gene for human TF begins at nucleotide 130 and ends at nucleotide 918.

FIG. 3*c,* right panel, presence of HEC-75 on 15 $\mu$m vessel (arrows) in normal basal ganglia (immunohistochemistry).

DETAILED DESCRIPTION OF THE INVENTION

Figure 2:
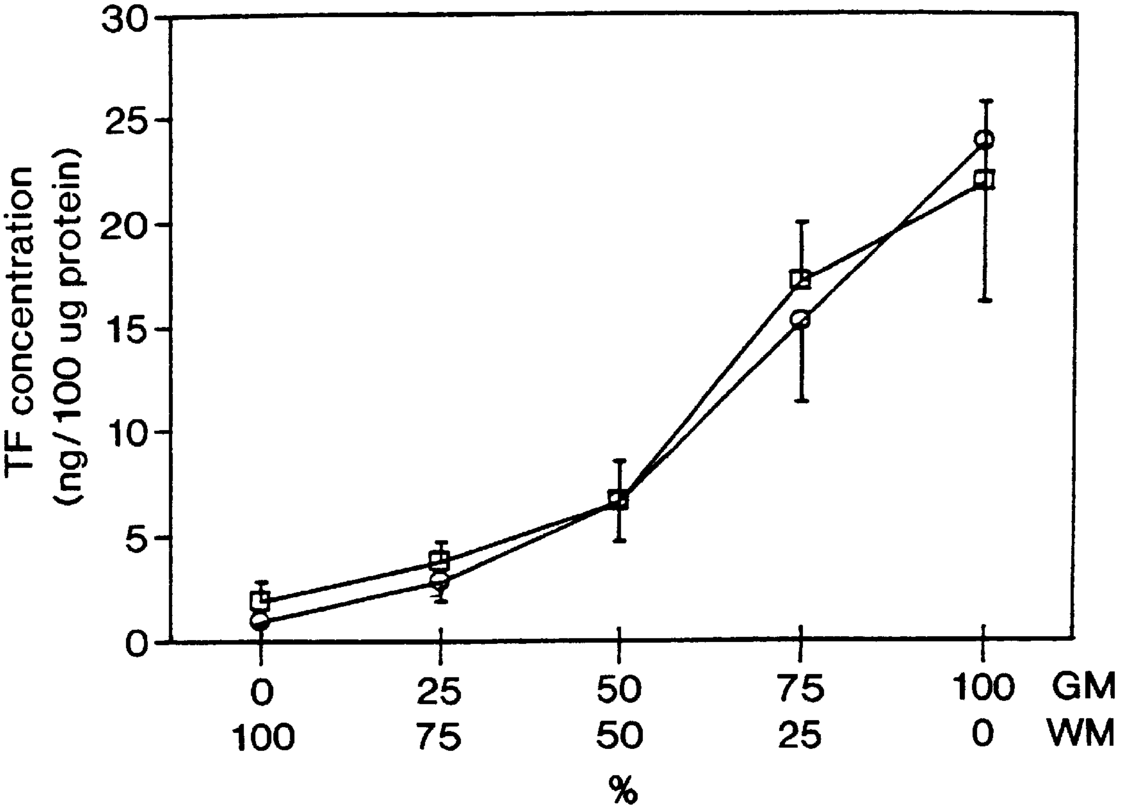
FIG. 2 shows the effect of mixing baboon white matter (WM) and gray matter (GM) on apparent human equivalent tissue factor concentration by one-stage clotting assay. Various amounts of WM (circles) are compared with equivalent amounts of protein as BSA (squares) so that total protein concentration was held constant at each data point (n-3 each).

The present invention provides a method of inhibiting tissue factor (TF) mediated reperfusion tissue damage in a subject, comprising administering to the subject a therapeutically effective amount of a TF inhibitor. TF binds coagulation factor VII or its derivative, factor Vila, to form a catalytically active complex to initiate coagulation. Thus, administration of a TF inhibitor, such as a monoclonal antibody or TF binding site polypeptide analog, would be useful in inhibiting initiation of the coagulation cascade by TF. The method of the invention can be used to prevent tissue damage due to reperfusion in various tissues such as central nervous system tissue (especially brain), myocardial tissue, or retinal tissue, for example.

The method of the invention is based on the unexpected discovery that TF plays a role in causing tissue damage following reperfusion. As used herein, the term "TF mediated reperfusion tissue damage", means damage caused after reperfusion that is a result of TF binding to factor VII/VIIa and initiation of the coagulation cascade. "Reperfusion" refers to the process whereby blood flow in the blood vessels is resumed after constriction or obstruction of flow, as in ischemia. Reperfusion may result following a naturally occurring episode, such as a stroke, or during a surgical procedure where blood flow in vessels is purposely blocked off. The constriction or occlusion of a blood vessel may occur as a result of a blood clot which blocks the blood flow in the vessel. Once the clot dissolves, either naturally or as a result of administration of a clot dissolving drug, blood begins to reflow through the vessel. At this point thrombosis, or new clot formation may occur. Under circumstances such as these, endothelial integrity is disrupted and, as a result, TF may begin the coagulation cascade and new clots form which lodge in smaller capillaries downstream from the original clot obstruction. It is during this reflow period that tissue damage occurs.

The method of the invention is useful for any animal in which TF could cause tissue damage following reperfusion. The preferred subject of the invention is a mammal, and most preferably a human.

The TF inhibitor of the invention can be administered parenterally by injection or by gradual perfusion over time. The inhibitor can be administered intravenously or intrathecally. Preferably the TF inhibitor is administered intravenously. Those of skill in the art will know of various other routes of administration which can be readily utilized in the method of the invention.

Preparations for parenteral administration are contained in a "pharmaceutically acceptable carrier". Such carriers include sterile aqueous or non-aqueous solutions, suspensions, and emulsions. Examples of non-aqueous solvents include propylene glycol, polyethylene glycol, vegetable oils such as, olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

The term "therapeutically effective" refers to an amount of TF inhibitor which is of sufficient quantity to decrease the ability of TF to bind Factor VII/VIIa, thereby reducing the initiation of the coagulation cascade. The dosage ranges for the administration of the inhibitor of the invention are those large enough to produce the desired effect. The dosage should not be so large as to cause adverse side effects, such as bleeding, unwanted cross-reactions, anaphylactic reactions and the like. Generally, the dosage will vary with the age, condition, sex, and extent of the disease in the patient and can be determined by one skilled in the art. The dosage can be adjusted by the individual physician in the event of any contraindications.

The TF inhibitor used according to the method of the invention may be a monoclonal antibody for example. The term "antibody" as used herein, refers to immunoglobulin molecules and immunologically active portions of immunoglobulin molecules, i.e., molecules that contain an antigen binding site or paratope. Examples of such antibody molecules are intact immunoglobulin molecules, substantially intact immunoglobulin molecules and those portions of an immunoglobulin molecule that contain the paratope, including those portions known in the art as Fab, Fab', $F(ab')_2$ and F(v).

Monoclonal antibody compositions useful in the method of the invention contain only one detectable species of antibody combining site capable of effectively binding TF, although mixtures of monoclonal antibodies of different epitopic specificity can be utilized which inhibit TF activation of clot formation. Thus, a monoclonal antibody composition useful in the present invention typically displays a single binding affinity for human TF even though it may contain antibodies capable of binding proteins other than TF.

An antibody composition useful in the present invention is an anti-peptide antibody characterized as containing antibody molecules that immunoreact with human TF and inhibit clot formation. For example, an antibody composition of the present invention may contain antibody molecules that immunoreact with TF and a polypeptide analog of the tissue factor binding site, and is capable of inhibiting the ability of TF to bind factor VII/VIIa.

The monoclonal antibodies useful in the present invention have the specificity of monoclonal antibodies TF8-5G9, TF9-5B7, and TF9-6B4, which are described in Morrissey, et al. (*Throm. Res.,* 52:247, 1988), and are available through the ATCC from hybridoma cell lines under accession numbers HB9382, (deposited Mar. 26, 1987) HB9381 (deposited Mar. 3, 1988) and HB9383, (deposited Mar. 26, 1987) respectively. However, any monoclonal antibody which immunoreacts with human TF in such a way that the antibody inhibits TF-initiated coagulation, is included within the method invention. Therefore, at a minimum, TF8-5G9, TF9-5B7, and TF9-6B4 and any other monoclonal with the specificity of these antibodies are included in the method of the invention.

An antibody composition useful in the present invention can be produced using various production systems well known in the art, such as by initiation a monoclonal hybridoma culture comprising a hybridoma that secretes antibody molecules of the appropriate polypeptide specificity. The culture is maintained under conditions and for a period of time sufficient for the hybridoma to secrete the antibody molecules into the medium. The antibody containing culture medium is then collected and antibody molecules can be further isolated by well known techniques. Monoclonal antibodies useful according to the method of the invention can also be purified from ascites fluid or recombinantly cloned (Huse, et al., *Science,* 246:1275, 1989; Mullinax, et al., *Proc. Natl. Acad. Sci. USA,* 87:8095, 1990; Sastry, et al., *Proc. Natl. Acad. Sci., USA,* 86:3833, 1989).

Methods for generating hybridomas producing (secreting) antibody molecules having a desired immunospecificity, i.e., having the ability to immunoreact with a particular protein and/or polypeptide, are well known in the art. Particularly applicable is the hybridoma technology described by Niman, et al. (*Proc.Natl.Acad.Sci. USA,* 80:4949, 1983). The techniques of sensitization and/or immunization, cell fusion, ascites production, selection of mixed hybridomas, or subcloning of monoclonal hybridomas are generally well known in the art. Attention is directed to Koprowski, et al., U.S. Pat. No. 4,172,124, Koprowski, et a., U.S. Pat. No. 4,196,265, or Douillard, J. Y. and Hoffman, T., *Basic Facts about Hybridomas,* in *Compendium of Immunology,* Vol. 11, L. Schwartz, ed. (1981), which are herein incorporated by reference.

In general, the purified epitopic peptides have a cystine attached at the C-terminus to permit unidirectional attachment of the synthetic peptide to an immunogenic protein through a connecting bridge, for example, maleimidobenzoylated (MB)-keyhole limpet hemocyanin (KLH). Other immunogenic conjugates can also be used, for example, albumin, and the like. The resulting structure may have several peptide structures linked to one molecule of protein.

Somatic cells derived from a host immunized with the synthetic peptides can be obtained by any suitable immunization technique. The host subject is immunized by administering the antigen, usually in the form of a protein conjugate, as indicated above, by any suitable method, preferably by injection, either intraperitoneally, intravenously, subcutaneously, or by intra-foot pad. Adjuvants may be included in the immunization protocol.

The initial immunization with the protein bound antigen can be followed by several booster injections given periodically at intervals of several weeks. The antibody contained in the plasma of each host can then be tested for its reactivity with the immunizing polypeptide of the invention. The host having the highest response is usually most desirable as the donor of the antibody secreting somatic cells used in the production of hybridomas. Alternatively, hyperimmunization can be effected by repeatedly injecting additional amounts of peptide-protein conjugate by intravenous and/or intraperitoneal route.

The isolation of hybridomas producing monoclonal antibodies that can be used according to the method of the invention can be accomplished using routine screening techniques which permit determination of the elementary reaction pattern of the monoclonal antibody of interest. Thus, if a monoclonal antibody being tested binds with TF to block the coagulation cascade or a TF binding site polypeptide analog of the invention, then the antibody being tested and the antibody produced by the hybridomas of the invention are equivalent.

Alternatively, since the invention teaches the use of TF binding site polypeptide analogs or amino acid sequences which are specifically required for binding of the preferred monoclonal antibodies of the invention, it is now possible to use these peptides for purposes of immunization to produce hybridomas which, in turn, produce monoclonal antibodies specific for the polypeptide. This approach has the added advantage of decreasing the repertoire of monoclonal antibodies generated by limiting the number of antigenic determinants presented at immunization by the polypeptide. The monoclonal antibodies produced by this method can be screened for specificity using standard techniques, for example, by binding polypeptide to a microtiter plate and measuring binding of the monoclonal antibody by an ELISA assay.

To identify other monoclonal antibodies having the specificity for binding TF in such a way that formation of TF:factor VII/VIIa complex and initiation of coagulation is blocked, a competitive inhibition assay can be performed. A monoclonal antibody useful for the method of the invention will compete with factor VII/VIIa for a binding site on TF. Human tissue factor-mediated binding of factor VII to the surface of J82 bladder carcinoma cells has been well characterized (Fair, et al., *J. Biol. Chem.,* 262:11692 1987) and these cells are useful for such an assay. The effects of a candidate monoclonal antibody useful in the method of the invention on the assembly of the cell surface TF:VII/VIIa complex can be directly evaluated by preincubating J82 cells, or other cells known to express cell surface TF, with the candidate antibody and then detecting the specific binding of labeled factor VII/VIIa. The specific binding of factor VII/VIIa to TF in the presence of candidate monoclonal antibody is compared to specific binding of factor VII/VIIa occurring in the absence of antibody. To facilitate detection of binding, factor VII/VIIa can be labeled with a radioisotope, such as $^{125}$l, or an enzyme which can be detected by appropriate reagents. Other labeling techniques and detectable labels will be apparent to those of skill in the art.

It is also possible to determine, without undue experimentation, if a candidate monoclonal antibody has the same specificity as a preferred monoclonal anti-body of the invention by ascertaining whether the former prevents the latter from binding to TF or the TF binding site polypeptide analog described for use in the invention. If the monoclonal antibody being tested competes with the preferred monoclonal antibody of the invention, as shown by a decrease in binding by the preferred monoclonal antibody of the invention, then it is likely that the two monoclonal antibodies bind to the same, or a closely related, epitope.

Still another way to determine whether a candidate monoclonal antibody has the specificity of a preferred monoclonal antibody of the invention is to pre-incubate the candidate monoclonal antibody of the invention with a TF binding site polypeptide analog with which the preferred monoclonal antibody is normally reactive, and then add the preferred monoclonal antibody to determine if the preferred monoclonal antibody is inhibited in its ability to bind the antigen. If the preferred monoclonal antibody is inhibited then, in all likelihood, the candidate monoclonal antibody has the same, or a closely related, epitopic specificity as the preferred monoclonal antibody of the invention.

While the in vivo use of a monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the TF coagulation inhibiting efficacy of the donor antibody. One way in which it is possible to circumvent the likelihood of an adverse immune response occurring in the host is by using chimeric antibodies (Sun, et al., *Hybridoma,* 5 (Supplement 1): S17, 1986; Oi, et al., *Bio Techniques,* 4(3): 214, 1986). Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic specificity, and the variable domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from a hybridoma of the invention and $C_H$ and $C_L$ domains coded for with DNA isolated from a human leukocyte.

Under certain circumstances, monoclonal antibodies of one isotype might be more preferable than those of another in terms of their diagnostic or therapeutic efficacy. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proc. Natl. Acad. Sci., U.S.A.,* 82:8653, 1985; Spira, et al., *J. Immunol. Methods,* 74:307, 1984). Thus, the preferred monoclonal antibodies of the invention would include class-switch variants having specificity for a TF binding site polypeptide analog of the invention.

The isolation of other hybridomas secreting monoclonal antibodies with the specificity of the preferred monoclonal antibodies of the invention can also be accomplished by one of ordinary skill in the art by producing anti-idiotypic antibodies (Herlyn, et al., *Science,* 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibody produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

The method of the invention includes not only monoclonal antibody TF inhibitors, but also human tissue factor binding site polypeptide analogs. Polypeptide analogs useful in this invention can inhibit TF mediated reperfusion tissue damage by binding to factor VII/VIIa and forming an inactive complex thereby inhibiting initiation of coagulation. The polypeptide analog should contain no more than about 50 amino acid residues, usually fewer than about 35, and preferably fewer than about 25 amino acid residues, and should contain at least about 10 residues.

A polypeptide analog useful in the invention is a human TF binding site polypeptide analog characterized by its ability to competitively inhibit the binding of TF to blood coagulation factor VII/VIIa. Preferably, the binding site analog polypeptide should bind factor VII/VIIa without producing an activated complex, i.e., without initiating coagulation.

Figure 3A:
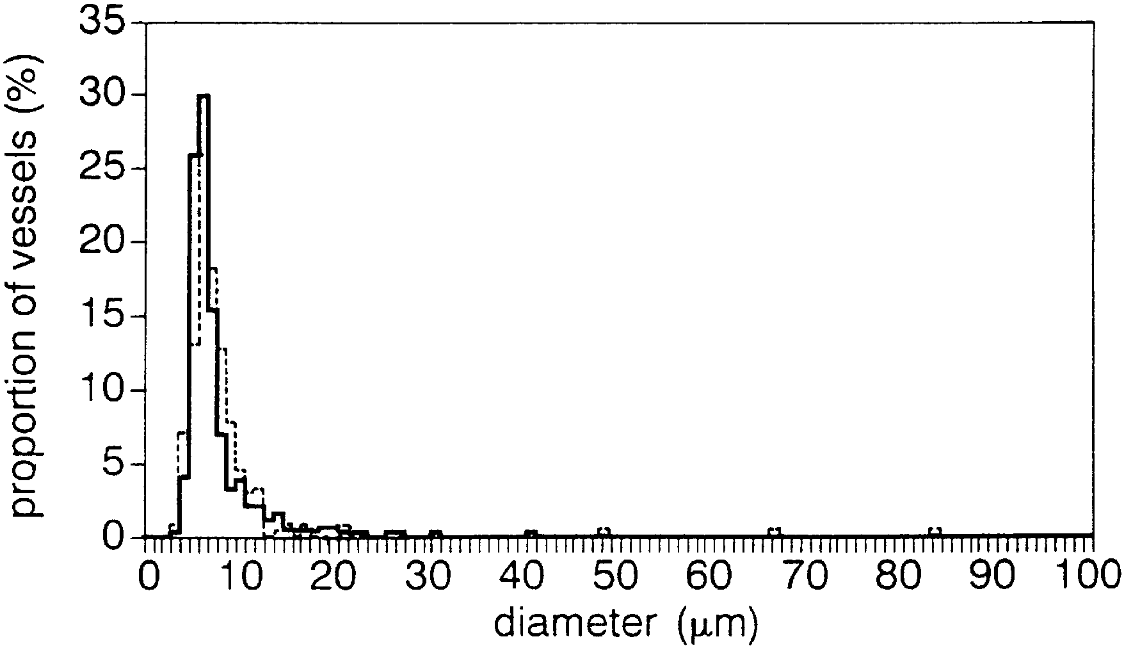
FIGS. 3*a,* 3*b*-1 and 3*b*-2 shows the distribution of microvascular diameters from 1 $\mu$m thick section (broken line) relative to the endothelial epitope CD31 in normal basal ganglia (solid line) in a baboon model.
Figures 1, 3B:
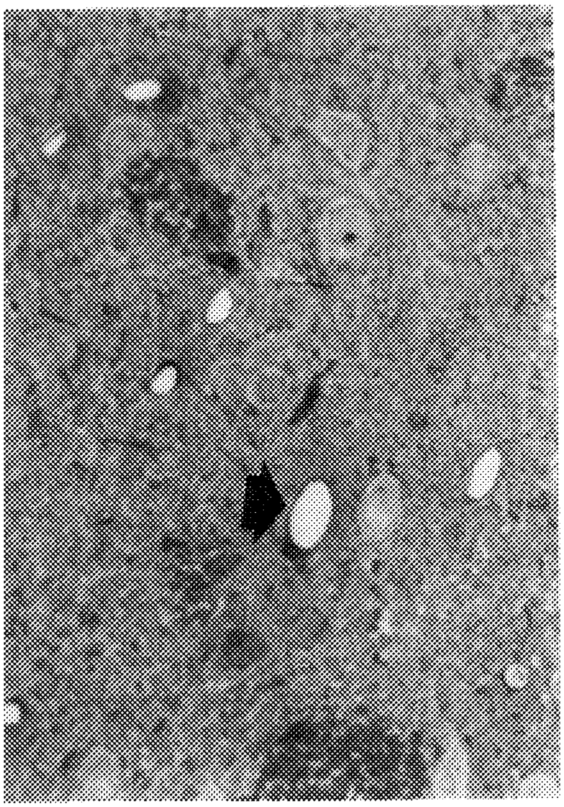
FIG. 3*b* (inset), left panel, microvessels of normal basal ganglia (histology, toluidine blue stain). 15 $\mu$m vessel indicated by arrow.

In a preferred embodiment, the human TF binding site analog includes at least the following amino acid residue sequence:

—VNQVYT—(SEQ ID NO: 1), representing amino acid residues 30–35 as shown in FIG. 1 (SEQ ID NO: 20). More preferably, the TF binding site analog includes at least the following amino acid residue sequences:

—VNQVYTVQIST—(SEQ ID NO: 20); or

—LYYWKSSSSGKKT—(SEQ ID NO: 3).

These sequences represent human TF amino acid residues 30–40 and 155–167, respectively, as shown in FIG. 1 (SEQ ID NO: 20).

Even more preferably, a human TF binding site analog includes an amino acid residue sequence selected from the group consisting of:

H—EPKPVNQVYTVQISTKSGDWKSKC—OH (SEQ ID NO: 4), and

H—VFGKDLIYTLYYWKSSSSGKKT—OH, (SEQ ID NO: 5)

representing amino acid residues 26–49 and 146–167, respectively, as shown in FIG. 1.

Other preferred binding site polypeptide analogs include those whose amino acid residue sequences are shown in Table 1.

TABLE 1

| Designation | Amino Acid Residue Sequence |
|---|---|
| H—SSSGKKTAKTNTNEFLIDVDKGENYCFSV—OH(SEQ ID NO:6); | p161–189 |
| H—SGTTNTVAAYNLTWKSTNFKTILEWEPKPV—OH(SEQ ID NO:7); | p1–30 |
| H—TKSGDWKSKCFYTTDTECDLTDEIVKDVKQTY—OH(SEQ ID NO:8); | p40–71 |
| H—KSGDWKSKC—OH(SEQ ID NO:9); | p41–49 |
| H—ECDLTDEIVKDVKQTY—OH(SEQ ID NO:10); | p56–71 |
| H—LARVFSYPAGNVESTGSAGEPLYENSPEFTPYLC–OH(SEQ ID NO:11); | p72–104C[a] |
| H—YENSPEFTPYLETNLGQPTIQSFEQVGTKV—OH(SEQ ID NO:12); | p94–123 |

TABLE 1-continued

| Designation | Amino Acid Residue Sequence |
|---|---|
| H—QAVIPSRTVNRKSTDSPVEC–OH(SEQ ID NO:13); | p190–209 |
| H—EWEPKPVNQVYT—OH(SEQ ID NO:14); | p24–35 |
| H—RDVFGKDLIYTLYYWK—OH(SEQ ID NO:15); | p144–159 |
| H—IYTLYYWKSSSSGKKTAK—OH(SEQ ID NO:16); | p159–169 |
| H—YWKSSSSGKKTAK—OH; and(SEQ ID NO:17) | p157–169 |
| H—SSSGKKTAKTNTNEFLIDVDKGENYCFSV—OH(SEQ ID NO:18), | p161–189 |

[a]The “C” indicates a cysteine residue was added to the indicated sequence as a linker for protein conjugation.

Polypeptides useful in the method of the invention include the polypeptides shown in Table 1 and conservative variations thereof. The term “conservative variation” as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term “conservative variation” also includes the use of a substituted amino acid in place of an unsubstituted parent amino acid provided that antibodies raised to the substituted polypeptide also immunoreact with the unsubstituted polypeptide. Therefore, as long as the polypeptide is able to compete with native TF for binding to factor VII/VIIa it is included in the invention. “Functional fragments” refers to any portion of the polypeptide analog which, as a result of conservative variations or other various changes, such as non-conservative variations, insertions, deletions and substitutions, is still able to inhibit TF from binding factor VII/VIIa.

When a polypeptide of the present invention has a sequence that is not identical to the sequence of native TF binding site because one or more conservative or non-conservative substitutions have been made, usually no more than about 20 percent and of the amino acid residues are substituted.

The ability of a polypeptide useful in the method of the invention to inhibit TF-initiated coagulation can be assayed by incubating the TF binding site polypeptide analog in question in the presence of factor VII/VIIa and calcium ions, and then adding the mixture to factor VII/VIIa-deficient plasma in the presence of TF and evaluating clotting times.

Alternatively, to identify other TF binding site polypeptide analogs having the specificity for binding factor VII/VIIa in such a way that formation of a TF:factor VII/VIIa complex and initiation of coagulation is blocked, a competitive inhibition assay can be performed. A TF binding site polypeptide useful for the method of the invention will compete with TF for a binding site on factor VII/VIIa. Therefore, it is possible to determine, without undue experimentation, if a polypeptide analog has the same specificity as a preferred polypeptide analog of the invention by ascertaining whether the analog prevents the TF from binding factor VII/VIIa. If a polypeptide being tested competes with a preferred polypeptide of the invention, as shown by a decrease in binding by TF or the preferred polypeptide of the invention, then the polypeptide analog is encompassed by the invention.

Another way to determine whether a polypeptide analog has the specificity of a preferred polypeptide analog of the invention is to pre-incubate the polypeptide being tested with factor VII/VIIa and then add the preferred polypeptide to determine if the polypeptide being tested inhibits the ability of the preferred polypeptide to bind factor VII/VIIa. If the polypeptide being tested inhibits the ability of the preferred polypeptide to bind factor VII/VIIa, then, in all likelihood, it has the same, or closely related, specificity as a preferred TF binding site polypeptide of the invention and is encompassed by the claims.

A polypeptide useful in the method of the invention can be synthesized by any technique known to those skilled in the art. These peptides can be synthesized by such well known solid phase peptide synthesis methods as described by Merrifield, *J.Am.Chem.Soc.* 85:2149, 1962, and Stewart and Young, *Solid Phase Peptides Synthesis,* (Freeman, San Francisco, 1969, pp. 27–62), using a copoly (styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0 C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

During or after the synthesis, reactive amino acids may be protected by various blocking groups, for example, cysteines may be blocked by 3,4-dimethylbenzyl (DMB) groups, arginines and histidines by tosyl (TOS) groups, aspartic acid and glutamic acids by benzyl (Bzl) groups, and lysines by the 2-chlorobenzylo-xycarboxyl (2-CBZ) groups. Other protective blocking groups are well-known, and can be used in the present invention. Those of ordinary skill in the art will know of other techniques for peptide synthesis, or can readily ascertain such techniques, without resorting to undue experimentation.

Alternatively, the polypeptides useful in the invention can be produced using recombinant techniques commonly known to those of skill in the art (see, for example, *Current Protocols in Molecular Biology,* Ausubel, et al., eds., Wiley Interscience Press, 1989, incorporated herein by reference).

The method of the invention is useful for inhibiting TF-mediated reperfusion damage in a variety of tissues. For example, the invention would be useful for inhibiting TF-mediated reperfusion damage in the tissue of the central nervous system (CNS) or tissue of the myocardium. Exemplary CNS and myocardial tissues include brain tissue and heart tissue, respectively. A common situation where clot formation, occlusion of a blood vessel, and reperfusion may occur is during a stroke, when a blood clot forms and blocks a blood vessel in the brain. Additionally, with a myocardial infarction, a clot may form in the vessels or arteries of the heart. In either situation, the use of a TF inhibitor in the method of the invention would be useful to inhibit TF-mediated reperfusion damage such as that which occurs as a consequence of recanalization of the parent blood vessel.

The following examples are intended to illustrate but not limit the invention. While they are typical of those that might be used, other procedures known to those skilled in the art may alternatively be used.

EXAMPLE 1

A. Monoclonal Antibodies (Moab)

The preparation and purification of the murine anti-human TF monoclonal antibodies TF9-6B4, TF8-6G9, TF8-11 D 12, TF9-6B4, TF9-8E8, TF9-10H10, and TF9-9C3, and the preparation of relipidated human brain TF and non-relipidated TF have been described previously (Morrissey JH, et al., *Thromb Res,* 52:247–261, 1988; Morrissey JH, et al., *Thromb Res,* 50:481–493). The MoAb TIB115, a murine MoAb against the irrelevant SV40 large T viral antibody, was obtained from the American Type Culture Collective (Rockville, Md.). Baboon brain TF was purified as described by Taylor, et al. (Taylor FB, et al., *Circ Shock,* 33:127–134, 1991). HEC-75, a well-characterized MoAb against CD31 on endothelial cells, was from J. van Mourik (Van Mourik JA, et al., *J. Biol. Chem.* 260:11300–11306, 1985), and 152B-6, a well-characterized MoAb against the RGD sequence of von Willebrand factor, was from Z. Ruggeri (Berliner S., et al., *J. Biol. Chem.* 263:7500–7505, 1988).

B. Reagents

In these studies, PBS contained 100 mM $Na_2HPO_4NaH_2PO_4$ and 140 mM NaCl adjusted to pH 7.4, and TBS (for "TBS wash solution") consisted of 5 mM Tris-HCl, 0.9% NaCl. Blotto refers to a blocking solution consisting of 5% dry milk solids, 1% horse serum, 0.1% sodium azide in 10 mM Tris-HCl, 140 mM NaCl, adjusted to pH 7.4 (Johnson, et al., *Gen Anal. Techn.* 1:3–8, 1984). Plasmalyte® (Baxter Healthcare, Deerfield, Ill.) was employed for perfusion and contains, according to the manufacturer's label, $Na^+$140 mEq/l, $K^+$5 mEq/l, $Mg^{+2}$ 3 mEq/l $Cl^-$98 mEq/l, acetate 27 mEq/l, gluconate 23 mEq/l.

C. Tissue Sources

1. Non-Human Primate

Selected tissue specimens were obtained from the cortical gray and subjacent white matter, basal ganglia, cerebellum, cervical spinal cord, and femoral arteries from three adolescent male baboons (*Papio anubis/cynocephalus) weighing* 9.0–11.0 kg. The animals were conditioned and observed to be disease-free during a mandated standard quarantine period prior to entry into the study. The isolation and removal procedures were approved by the institutional Animal Research Committee, and were performed in accordance with standards published by the National Research Council (the Guide for the Care and Use of Laboratory Animals), the National Institutes of Health policy on Humane Care and Use of Laboratory Animals, and the USDA Animal Welfare Act. The principal investigator, veterinarian, and primate handling staff were present for all procedures.

Under pentothal $Na^+$anesthesia, a left occipital quadrant cranial window was extended caudally to the foramen magnum and rostrally by segmental removal of the cranium. Hemorrhage was minimal (10–20 ml) and controlled easily with bone wax. Perfusion of the superior thoracic and cranial structures was achieved by infusion of chilled (4° C.) perfusion fluid at 160–200 torr for 4 min (flow=600–800 ml/min) via left ventricular puncture with simultaneous clamping of the aorta and inferior vena cava, and venting of the right atrium. The perfusion fluid consisted of Plasmalyte®, 50 mg/ml bovine serum albumin (BSA, Sigma, St. Louis, Mo.), 2 lU/ml heparin, and 6.7 $\mu$M $Na^+$Nitroprusside (Fisher Scientific, Fair Lawn, N.J.) adjusted to 340 m0sm/l and pH 7.4. By a similar perfusion procedure, >99% of microvessels were free of blood elements (del Zoppo GJ, et al., *Stroke,* 22:1276–1283, 1991).

After removal of the dura, the brain, brain stem, and the $Cl_{1-3}$ portion of the spinal cord were excised in toto by two operators. One-centimeter coronal sections were subdivided at 4° C. and separate tissue specimens were: i) frozen directly in liquid $N_2$, or ii) embedded in Tissue-Tek® OCT compound (Miles Inc., Elkhart, Ind.) in individual 20mm× 25 mm cryomolds, frozen in 2-methylbutane/dry ice, and stored at −70° C.

2. Human

Portions of grossly normal-appearing temporal lobe cortex and associated white matter were obtained directly from four patients undergoing selective temporal lobectomy for intractable recurrent epileptic (complex partial) fits. Preoperative computerized tomographic (CT) and magnetic resonance imaging (MRI) scans failed to detect evidence of lesions in the affected temporal lobe. Intraoperative regional electroencephalographic recordings localized the epileptic focus. Tissues were processed directly within 2–5 min of removal and portions of cortex and subjacent white matter were carefully separated and suspended in chilled PBS for immediate homogenization. Other samples were subdivided and i) frozen directly, or ii) placed in OCT in individual cassettes and frozen as noted above for later immunohistochemical studies. Routine independent pathological examination of the surgical specimens demonstrated no abnormality in any specimen.

D. Tissue Homogenates

Frozen tissue specimens of baboon or human tissues were thawed to room temperature and suspended in 1 ml chilled TBS at 300 mg (wet weight)/ml chilled TBS. Individual tissues were homogenized in triplicate at 40° C. by 25 cycles with a Dounce homogenizer. All homogenates were adjusted to a protein concentration of 100 $\mu$g/ml for TF procoagulant and TF antigen (ELISA) determinations. Protein concentrations were determined by the BCA® protein assay (Pierce, Rockford, Ill.).

E. Assays for Tissue Factor (TF)

Assays for TF activity and antigen have been described (Morrissey JH, et al., *Thromb Res,* 52:247–261, 1988; Morrissey JH, et al., *Thromb Res,* 50:481–493, 1988; del Zoppo GJ, et al., *Thromb Haemost,* 65:682, 1991). TF-related procoagulant activity was determined with a $Ca^{+2}$-dependent one-stage clotting assay and confirmed by parallel inhibition of clotting with the anti-TF MoAb mixture TF8-11 D 12/TF9-6B4/TF9-8E8. Incubation mixtures of 100 $\mu$l pooled plasma, 50 $\mu$l tissue homogenate (or relipidated TF standard) at serial dilutions, and 50 pi TBS or MoAb anti-TF complex were activated with 100 $\mu$l $CaCl_2$ (20 mM, Ortho, Raritan, N.J.). Separate parallel studies were performed with the same reaction mixtures containing fixed contents of rabbit brain cephalin (RBC, Sigma, St. Louis, Mo.) prepared according to the manufacturer's instructions. All measurements were made in triplicate and in parallel with BBL® fibrometers (Bectin Dickinson, Cockeysville, Md.). Relative activity measurements (clotting times) were determined in the linear portions of the standard dilution curves for each sample (with or without RBC) relative to purified relipidated human TF. The results were converted to human TF antigen equivalent and normalized for protein content.

An amplified MoAb sandwich ELISA was used to quantitate tissue factor antigen levels in the homogenates. Flatbotom, 96-well polystyrene Immulon® microtiter plates (Dynatrech Laboratories, Chantilly, Va.) were coated with the primary (capture) antibody TF9-6B4 (10 μg/ml) in TBS at 4° C. overnight, blocked with Blotto for 2 hours at 37° C., and washed prior to use. Homogenates were diluted in Blotto/0.5% Triton X-100 and duplicate samples were incubated for 90 min at 37° C. followed by washing. TF antigen was detected by biotinylated TF8-5G9 (0.04 μg/ml), and streptavidin-conjugated alkaline phosphatase (BRL, Gaithersberg, Md.), followed by an ELISA iodonitrotetrazolium (INT) violet NADP-based Amplification System (BRL, Gaithersberg, Md.), with interposed washings. The colored end-product Formazan was measured at 490 nm with a programmed Dynatech ELISA microtiter plate reader. Relative quantities of primate TF were normalized as human TF equivalent per 100 μg protein. Homogenates from 2–3 specimens from each tissue were assayed in duplicate or triplicate, and repeated.

Standard curves from known concentrations of immunoaffinity purified human TF reconstituted in phospholipid vesicles containing 70% phosphatidylcholine and 30% phosphatidylserine (relipidated TF), and from non-relipidated immunoaffinity purified human brain TF were constructed for each one-stage procoagulant assay and ELISA, respectivley. A linear relationship between the procoagulant assay and ELISA determinations was established for relipidated purified human TF (linear regression coefficient (r)=0.9985). For the ELISA studies the same primary and secondary MoAb were used for human and baboon specimens.

F. Immunohistochemistry

Immunohistochemical studies were performed on fresh cerebral tissues prepared as cryostat sections (5 or 10 μm thickness). Sections were fixed with methanol for 3 min at 4° C., immersed in 100 mM glycine in TBS for 10 min, then rinsed three times with TBS wash solution, and subsequently incubated with Blotto for 30 min to reduce nonspecific binding. Fifty μl of the primary MoAb complex (murine anti-human MoAb TF9-10H10 and TF9-9C3 at 0.1 μg/ml each; HEC-75 at 1:200 dilution of ascites; TIB115 at 0.1 μg/ml; or 152B6 at 0.1 μg/ml) was incubated on each section for 120 min at 370° C. in a humidified chamber, followed by three TBS washes and subsequent incubation of biotinylated horse anti-mouse IgG (1:400 in reagent diluent; Vector Laboratories, Burlingame, Calif.) for 30 min at 37° C. The sections were sequentially incubated with 0.03% hydrogen peroxide in pure methanol for 20 min to block endogenous peroxidase activities and washed with tap water 2–3 min, followed by three TBS washes, then incubated with streptavidin horseradish peroxidase complex (Vector Laboratories) for 30 min at 37° C. followed by three PBS washes. Antibody-bound peroxidase was detected with the chromogen substrate 3-amino-9-ethyl carbazole (AEC Kit), freshly prepared at 0.02% in 20 mM sodium acetate buffer and 0.03% hydrogen peroxide and incubated for 10 min at 37° C. Sections were washed in tap water for 2–3 min and counter-stained with Mayer's hematoxylin (Biomeda Corporation, Foster City, Calif.) for 1.0–1.5 min, blued in saturated sodium bicarbonate solution, or were left unstained. All immunostained specimens were then mounted with clear mounting medium (Biomeda Corporation). The following immunohistochemical controls were routinely performed on each tissue type: i) deletion of the primary antibody, ii) deletion of the secondary antibody, iii) TIB115, iv) for TF a blocking control consisting of the anti-TF MoAb mixture and relipidated TF, and v) 152B-6. In the case of TF, incubation of tissue blocks at 20° C. for various times up to 2 hours did not increase TF intensity.

Additionally, 10 μm frozen sections of normal femoral arterial segments were fixed with acetone for 3 min at 4° C and incubated with the primary MoAb at 37° C. for 120 min. An FITC-labelled horse anti-murine IgG MoAb (Vector Laboratories) was used as the secondary antibody. Sections were viewed at 490 nm incident light.

G. Histological Studies

For comparison with sections prepared for immunohistochemistry, thick sections of perfused-fixed normal cortex and basal ganglia of a separate animal from a cohort previously described (del Zoppo, et al., *Stroke,* 22:1276, 1991) were examined. Perfusion with a suspension of colloidal gold (18–20 nm diameter) in Plasmalyte® (Baxter Healthcare, Deerfield, Ill.), 25 mg/ml BSA, 2 IU/ml heparin, 6.7 μM $Na_+$ nitropruside (Fisher Scientific, Fair Lawn, N.J.) adjusted to 340 m0sm/l with NaCl, and to pH 7.35 was followed by fixation with colloidal gold suspended in 2% paraformaldehyde/0.5% glutaraldehyde in 10 mM phosphate-buffered saline (del Zoppo GJ, et al., ibid). Tissue blocks were embedded in TAAB-812 epoxy resin (TAAB Laboratory Equipment, Ltd., Reading, UK), cut at 1 μm thickness, and stained with toluidine blue.

H. Video-Imaging Microscopy

The vascular association of CD31 and of TF was quantitated with the aid of a video-imaging system consisting of an image processing unit connected in-line with a Hamamatsu C2400-07 Newvicon NTSC video camera staged vertically on the light microscope (VIDAS; Kontron and Carl Zeiss, Munich, FRG). Minimum transverse diameters of peroxidase-stained vascular structures were computed with the resident linear measurement program, and the normalized data was presented in histogram form for each epitope (del Zoppo GJ, et al., *Stroke,* 22:1276–1283, 1991).

I. Statistical Comparisons

Data are presented in the literal form and as the mean±standard deviation. Statistical comparisons were performed with the Student's t-test (two-tailed) for unpaired series.

J. Parenchymal Distribution of Tissue Factor Antigen

Immunofluorescent studies confirmed the binding of TF9-10H10TF9-9C3 to adventitia (Drake T., et al., *Am J Pathol,* 134:1087–1097, 1989) and HEC-75 to the endothelial layer (Van Mourik JA, et al., *J. Biol. Chem.* 260:11300–11306, 1985) of the non-human primate femoral artery.

Diffuse binding of the anti-TF MoAb mixture to temporal lobe cortical gray matter was demonstrated in the four human subjects. The intensity of peroxidase stain (3+to 4+) was quite similar to that of published reports (Drake T., et al., *Am J Pathol,* 134:1087–1097, 1989; Fleck RA, et al., *Thromb Res,* 57:765–782, 1990).

The relative parenchymal distribution of TF was more difficult to discern in the primate; however, regional differences were apparent among the three animals (Table 2). Variation in the distribution of peroxidase stain was noted within each animal and among animals. In general, the peroxidase signal for TF in gray matter exceeded that of white matter in the cortex, basal ganglion, and spinal cord. TF antigen was not identified specifically with any cells of cortical layers I–VIB. A similar parenchymal distribution of TF antigen was noted in the basal ganglia sparing fiber tracts of the internal capsule. The gray matter parenchyma/vascular compartmentalization of TF distribution was most striking in the cervical spinal cord when TF antigen was associated with the central gray matter. In addition, TF was associated with the substantia gelatinosa and fibers of the dorsolateral tract. Anti-TF MoAb associated peroxidase stain was found on individual vessels in all cerebral tissues studied (see below).

TABLE 2

VARIATION IN TISSUE FACTOR DISTRIBUTION

| Region | Animal 1 | 2 | 3 |
|---|---|---|---|
| Cortex | | | |
| Gray Matter | + | + | ++ |
| White Matter | − | − | − |
| Basal Ganglion | | | |
| Gray Matter | + | ± | + |
| White Matter | − | − | − |
| Cerebellum | | | |
| Gray Matter | ± | − | ± |
| White Matter | − | − | − |
| Spinal Cord | | | |
| Gray Matter | + | ± | ++ |
| White Matter | − | − | − |

+ = Relative to peroxidase intensity of human cortical gray matter (3+ to 4+) (see text).
− = No evidence of peroxidase stain.

K. Relative Cerebral Tissue Content of Tissue Factor

To further quantitate regional differences in TF content, homogenates from normal frontal and temporal cortical gray and white matter, basal ganglion (containing the caudate nucleus, internal capsule, and putamen), and cerebellum were studied. Among the three primate sources, normalized TF content (ELISA) was significantly lower in cortical white matter than gray matter, while intermediate contents were obtained from samples of normal basal ganglia and cerebellum (Table 3).

Tissue factor content of human temporal lobe white matter (0.42±0.18 μg TF/100 μg protein) was also significantly less than that obtained from adjacent cortical gray matter (1.29±0.13 μg TF/100 μg protein) (2p <0.0001).

TABLE 3

VARIATION IN TISSUE FACTOR CONTENT

| Region<br>Cortex | TF Antigen (ng/100 μg protein)<br>Animal 1 | 2 | 3 |
|---|---|---|---|
| Gray Matter | 2.96 ± 0.19 | 1.63 ± 0.37 | 1.37 ± 0.40 |
| White Matter | 1.69 ± 0.71 | 0.29 ± 0.04 | 0.24 ± 0.09 |
| Basal Ganglian | 1.80 ± 0.04 | 0.84 ± 0.18 | 0.38 ± 0.13 |
| Cerebellum | 1.71 ± 0.42 | 0.56 ± 0.34 | 0.29 ± 0.12 |

The relative TF content distribution was confirmed when procoagulant activity was measured, as illustrated for animal number 2 (Table 4). White matter from the temporal lobe cortex contained significantly less procoagulant activity than the adjacent gray matter (2p <0.0001). The procoagulant activity in each sample was 96.5–98.5% inhibitable by the murine anti-TF MoAb combination TF8-11 D12/TF9-6B4/TF9-8E8, also known to block 99.8±0.1% human relipidated TF-associated procoagulant activity.

To test the possibility that the presence of white matter may contribute to decreased TF activity in gray matter samples, various proportions of gray and white matter homogenates were assayed for procoagulant activity. A monotonic increase in clotting time was observed with increasing proportion of white matter which indicated decreasing apparent TF content (FIG. 2). No difference in gray matter-dependent TF content between white matter nad albumin control was seen, with or without added cephalin. FIG. 2 shows the effect of mixing white matter (WM) and gray matter (GM) on apparent human-equivalent tissue factor concentration by one-stage clotting assay. Various amounts of WM (circles) are compared with equivalent amounts fo protein as BSA (squares) so that total protein concentration was held constant at each data point (n-3 each). All assays were performed with added cephalin.

TF activity/antigen ratios differed among animals, but were quite consistent among tissues within each animal: 0.7–5.9 for subject 1, 3.0–6.8 for subject 2, and 16.4–46.1 for subject 3.

TABLE 4

VARIATION IN TISSUE FACTOR ACTIVITY

| Region | N | TF Antigen (ng/100 μg protein) | TF Activity (ng/100 μg protein) | Activity/Antigen Ratio | TF Inhibition (%) |
|---|---|---|---|---|---|
| Cortex | | | | | |
| Gray Matter | 12 | 1.63 ± 0.37⁺ | 11.1 ± 1.1* | 6.81 | 97.9 ± 0.9 |
| White Matter | 12 | 0.29 ± 0.04⁺ | 0.9 ± 0.6* | 3.04 | 98.5 ± 0.9 |
| Basal Ganglian | 12 | 0.84 ± 0.18 | 4.8 ± 2.1 | 5.70 | 98.5 ± 0.9 |
| Cerebellum | 12 | 0.56 ± 0.34 | 2.8 ± 0.4 | 4.96 | 96.5 ± 1.2 |

From cerebral tissue homogenates of animal 2 (see text).
+,*= Gray matter/white matter comparisons, 2p < 0.0001

L. Vascular Distribution of Tissue Factor Antigen

Figures 2, 3B:
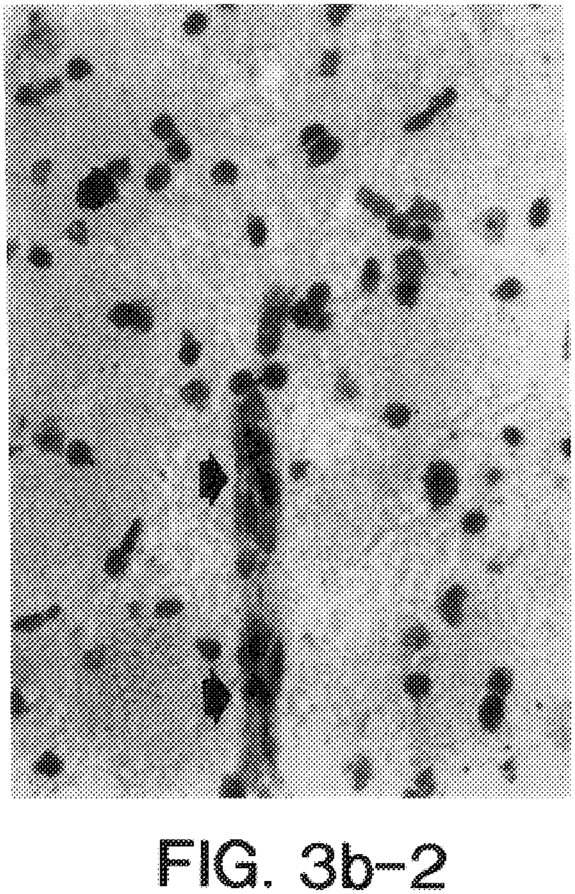

TF antigen was found in specific segments of the primate cerebral microvasculature when compared to the ubiquitous endothelial cell receptor CD31. HEC-75 clearly signalled microvessels of all sizes, including capillaries (4.0–7.5 μm daimeter), in a vascular distribution identical to that of histological preparations of the same territory (basal ganglian, FIG. 3). FIG. 3 shows the distribution of microvascular diameters from 1 μm thick sections (broken line) relative to the endothelial epitope CD31 in normal basal ganglia (solid line) (animal 1). Inset: Left panel, microvessels of normal basal ganglia (histology, toluidine blue stain). 15 μm vessel indicated by arrow. Right panel, presence of HEC-75 on 15 μm vessel (arrows) in normal basal ganglia (immunohistochemistry).

Figure 4A:
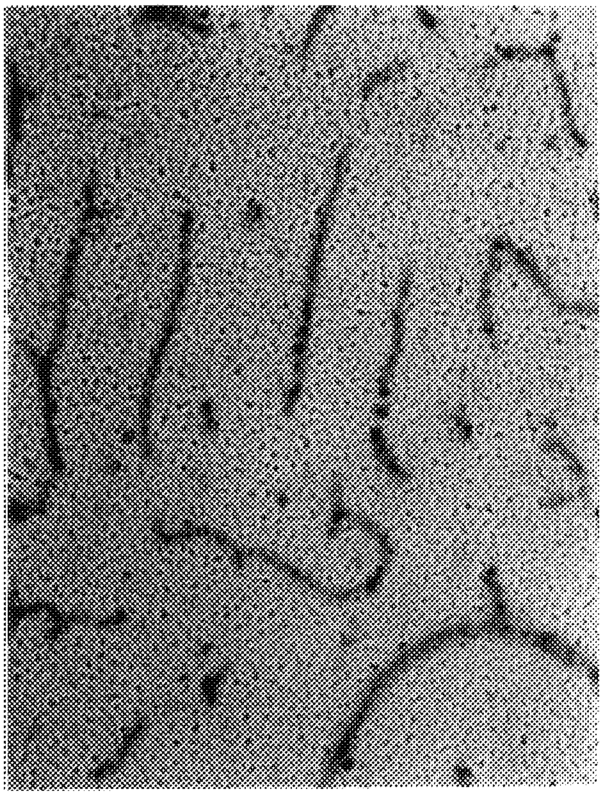
FIGS. 4*a* and 4*b* show the vascular distribution of CD31 as compared to tissue factor in a baboon model.
Figure 4B:
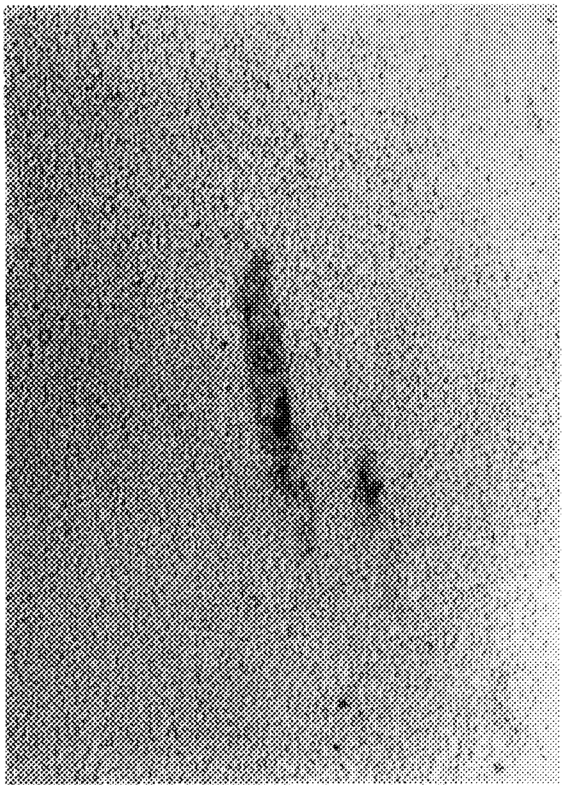
Figure 5A:
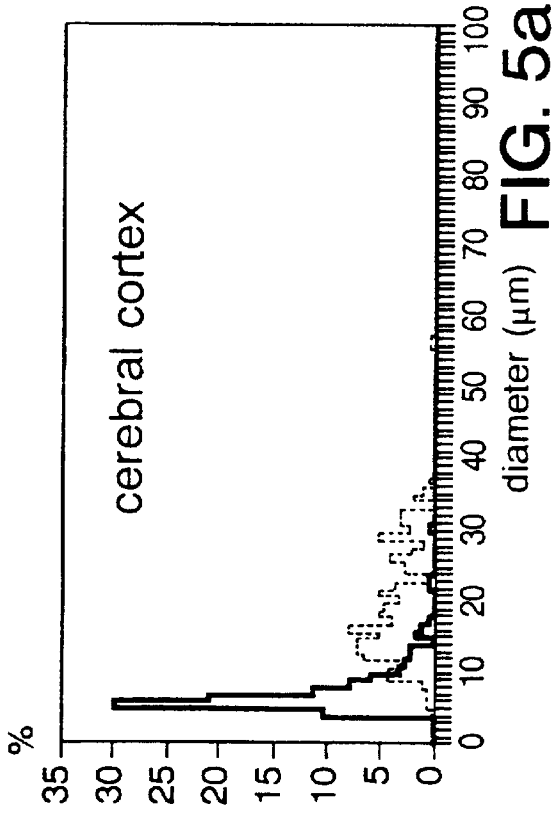
FIG. 5*a* to 5*b* show microvessel tissue factor distribution (broken lines) in normal baboon cortex, basal ganglia, cerebellum, and spinal cord, relative to the endothelial epitope CD31 (solid lines).
Figure 5B:
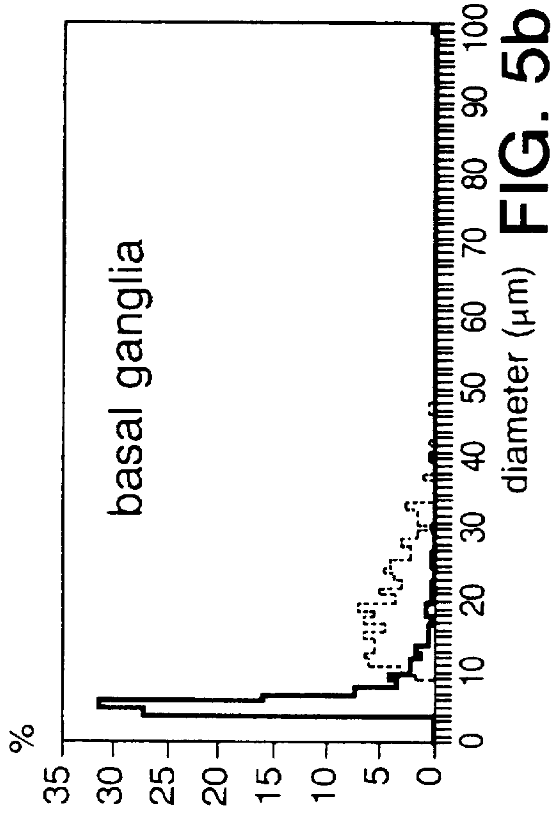
Figure 5C:
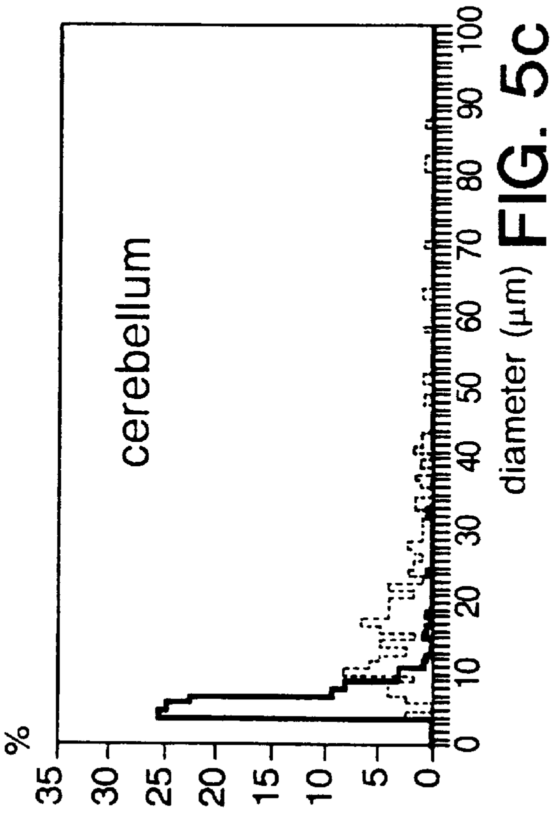
Figure 5D:
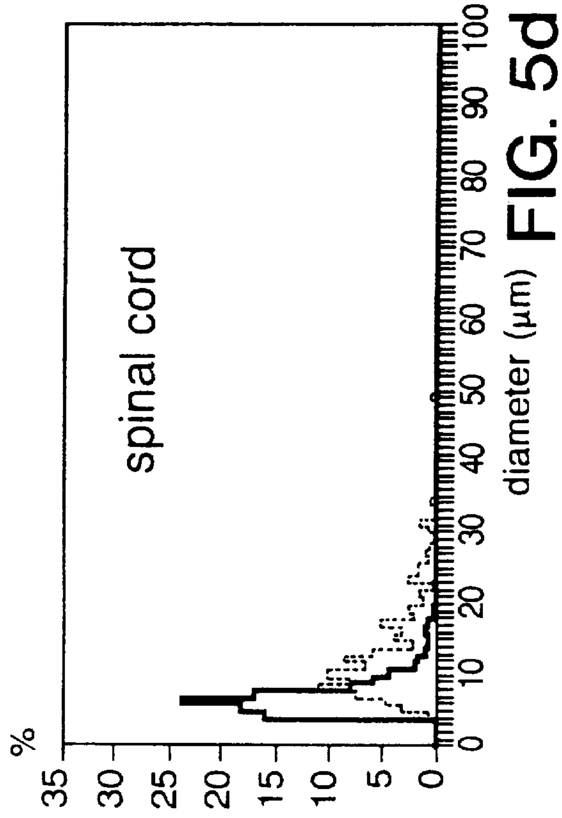

The vascular distribution of CD31 was distinct from that of TF (cortex, FIG. 4). FIG. 4 shows: Left panel, presence of HEC-75 (anti-CD31) in gray matter of normal temporal cortex. Right panel, TF9-10H10/TF9-9C3 (anti-tissue factor) in adjacent section of temporal lobe gray matter (animal 3). Magnification bar=20 μm. TF antigen was predominantly associated with vessels of >10 μm diameter in the basal ganglia, sparing capillaries in both regions (FIG. 5). FIG. 5 shows microvessel tissue factor distribution (broken line) in normal cortex, basal ganglia, cerebellum, and spinal cord relative to the endothelial epitope CD31 (solid line). TF was associated with capiallaries in 0.5, 0.0, 6.5, and 26.5% of these tissues, respectively (animal 3). Identical distributions were observed in the cortical gray and white matter, cerebellum, and cervical spinal cord. TF was found primarily on the central axial microvessels of the cerebellar follae, but involved smaller vessels throughout the spinal cord gray matter and long fiber tracts. The proportion of vessels of capillary diameter containing TF was tissue-related and followed the distribution: cortex= basal ganglian<cerebellum<spinal cord. Whether TF antigen was confined to the subendothelial muscular layers of the microvasculature or was associated with subjacent neuronal structures could not be determined.

EXAMPLE 2

EXPERIMENTAL MODEL OF REPERFUSION

Twelve adolescent male baboons (Papio anubis/ cynocephalus) weighing 7.7–14.0 kg were utilized for the present studies. All animals lacked evidence of disease during a quarantine period of one month prior to entry into this study. The procedures used throughout this study were approved by the institutional Animal Research Committee and were performed in accordance with standards set by The National Research Council (the Guide for the Care and Use of Laboratory Animals), The National Institutes of Health Policy on Humane Care and Use of Laboratory Animals, and the USDA Animal Welfare Act.

Preparation of the non-human primate model of right MCA occlusion and reperfusion, and surgical implantation of the MCA occlusion device (Mentor Corporation, Goleta, Calif.) have been previously described in detail (del Zoppo GJ, et al., *Stroke,* 22:1276–1283, 1991; Mori E, et al., *Stroke,* 23:712–718, 1992; del Zoppo GJ, et al., *Stroke,* 17:1254–1265, 1986). Halothane anesthesia was administered as 3 to 5% induction followed by 1.5 to 2.0% maintenance. The surgical procedure typically lasted 1.2–1.5 hours. Following surgical recovery, all animals were allowed a 7-day interval prior to entry into the experimental protocol. All animals entered into the study were clinically free of infection or apparent inflammation and had normal neurological function (score=100).

In a non-randomized open study, 6 animals were assigned to receive TF9-6B4 by intravenous infusion, and 6 animals were to receive no intervention and served as a control group. All subjects were awake. The treatment group received a single 10 mg/kg intravenous infusion of TF9-6B4 5 minutes prior to MCA occlusion. Thereafter, the right MCA was occluded by inflation of the extrinsic MCA balloon. Following a 3-hour period of MCA occlusion, the balloon was deflated to allow reperfusion of the MCA territory.

Each experiment was terminated 60 minutes following MCA balloon deflation by perfusion-fixation with carbon tracer at high mean arterial pressure. Perfusion fixation by left ventricular puncture was conducted under pentothal Na+(15 mg/kg infusion) anesthesia and mechanical ventilation as previously described (del Zoppo GJ, et al., *Stroke,* 22:1276–1283, 1991; Mori E, et al., *Stroke,* 23:712–718, 1992; del Zoppo GJ, et al., Stroke, 17:1254–1265, 1986). Isosmotic perfusion flush solution consisted of 25 gm/1 bovine serum albumin (BSA; Sigma, St. Louis, MO), 2,000 lU/l heparin, and 6.7,$\mu$m Na+nitroprusside (Fisher Scientific, Fair Lawn N.J.) in Plasmalyte® (Baxter Healthcare, Deerfield, Ill.) adjusted to 340 m0sm/l with NaCl, pH 7.4, and 4° C. to allow wash-out of all blood elements under antithrombotic conditions. The carbon suspension/fixative solution consisted of india ink (Pelikan Fount India, Pelikan AG, Hannover, FRG) diluted 1:1, v/v in Plasmalyte®/paraformaldehyde (2%)/glutaraldehyde (0.5%) adjusted to 340 m0sm/l and chilled to 4° C. Prior to dilution, the india ink was centrifuged at 500–g for 10 minutes to eliminate large carbon aggregates. The perfusion flush solution was delivered at 180–210 torr (700–800 ml/min flow) for 4.0 minutes and was followed immediately by tracer perfusion-fixation at constant pressure for 17.0 minutes. A perfusion circuit was obtained by incising the right atrium to allow egress of the perfusate.

Following perfusion/fixation the exposed brain was immersed in alcohol-formaldehyde-acid (AFA) solution, consisting of 87% ethanol, 10% formaldehyde, 3% glacial acetic acid (v/v), for 7 days (Mori E, et al., *Stroke,* 23:712–718, 1992). Two millimeter coronal sections were immersed for a further week in AFA solution. Tissue blocks (1.0 cm×1.0 cm×0.2 cm) from stereo-anatomically identical sites of the left and right basal ganglia and from the temporal lobe in the left (non-ischemic) side were embedded in glycol methacrylate (Polysciences, Inc., Warrington, Pa.), sectioned to 10 $\mu$m thickness, and stained with basic fuchsin/ methylene blue.

The relative number and minimum transverse diameters of carbon-filled (patent) microvascular structures in sections from the normal and post-I/R territories were determined with a computerized video-imaging system consisting of a Hamamatsu C2400-07 Newvicon NTSC video camera (Hamamatsu Photonics, Hamamatsu, Japan) staged vertically on the light microscope (VIDAS; Kontron and Carl Zeiss, Munich, FRG) and an image processing unit. Ninety non-overlapping 526.1 $\mu$m×491.4 $\mu$m images at 200x optical magnification in a 9×10 field matrix (25 $mm^2$) were automatically processed from each section. As previously, the sections were taken at 30 $\mu$m intervals from one another, such that an identical number of fields (3 to 8 sections) from each of the paired basal ganglia yielding up to 2,000 vessels in the left control basal ganglia were analyzed. Reproducibility and reliability data acquired with this video-image processing system have been reported previously (del Zoppo GJ, et al., *Stroke,* 22:1276–1283, 1991).

Adequacy criteria for complete analysis of microvascular patency have been noted previously, (Mori E, et al., *Stroke,* 23:712–718, 1992) and have been applied to this analysis. In this experiment the ratio of all microvessels in the left (normal) basal ganglia to the left temporal cortex (layers I–VI) was 0.59±0.27 (n- 6) and 0.60±0.23 (n- 6) for control and treated animals, respectively. This compares favorably with previous observations in which the distribution and morphology of patent microvessels in the left basal ganglia were judged excellent. (Mori E, et al., *Stroke,* 23:712–718, 1992).

Relative microvascular patency in the basal ganglia was expressed as "percent reflow," the ratio of the number of carbon-containing microvessels in the ischemic to control basal ganglia normalized per 1.0 $cm^2$ expressed per 100 vessels (Mori E, et al., Stroke, 23:712–718, 1992). Definitions of microvascular size were used to pool the continuum of vessel diameters into discrete vessel size classes: i) capillaries, vessels of 4.0–7.5 $\mu$m diameter; ii) precapillary arterioles (metarterioles) and postcapillary venules, vessels of 7.5–30 $\mu$m diameter; iii) small arterioles and connecting venules, vessels of 30–50 $\mu$m diameter; and iv) muscular arterioles and venules, vessels of 50–100 $\mu$m diameter (Ham AW, et al., *Histology,* ed 8th, pp 581–613, 1979; Williams PL, et al., *Gray's Anatomy, ed* 36th, pp 622–629, 1980). Neurological function was assessed according to the quantitative (100-point) scale suggested by Spetzler and colleagues. (del Zoppo GJ, et al., *Stroke,* 22:1276–1283, 1991; Mori E, et al., *Stroke,* 23:712–718, 1992; del Zoppo GJ, et al., *Stroke,* 17:1254–1265, 1986; Spetzler RF, et al., *J Neurosurg,* 7:257–261. 1980). This scale is weighted toward unilateral motor function loss.

The anti-TF MoAb, TF9-6B4, was purified from cell culture by protein A affinity chromatography. The culture supernatant was diluted 1:1 with binding buffer (0.1M glycine, 3M NaCl, pH 8.9) and passed over a protein A (IPA 300, Repligen, Boston, Mass.) column to bind murine IgG. Antibody was eluted with 50 mM acetate, 100 mM NaCl (pH 4.0). Elution was monitored by UV absorbance. The protein A column eluate was loaded onto a G-25 sepharose (Pharmacia, Stockholm) column equilibrated with 50/50 PBS buffer (50 mM phosphate, 50 mM NaC1, pH 7.0) to exchange buffers. Following buffer exchange, the antibody was filter-concentrated to 5–6 mg/ml using a Membrex Benchmark® Rotary Biopurification System. Monoclonal antibody in 50/50 buffer was then passed over DEAE Sepharose FF (Pharmacia, Stockholm) in non-bonding mode to reduce LPS and DNA contamination. The final product was sterilized by filtration through a 0.2 micron filter. Purified monoclonal antibody was greater than 90% pure by SDS-PAGE analysis and had endotoxin levels of less than 2 EU/ml by LAL chromogenic assay (Whittaker, Walkersville, Md.). Material from a single lot was supplied by R. W. Johnson Pharmaceutical Research Institute (La Jolla, Calif.).

Peripheral blood samples for TF9-6B4 (murine immunoglobulin) level determinations were obtained by venipuncture and drawn into Na+heparin (100 lU/ml) at various times: prior to TF9-6B4 infusion and MCA occlusion, and at 10, 60, 120, 180 and 240 minutes after MCA occlusion. Plasmas from each sample were frozen and stored at 70° until assay. Levels of murine $IgG_1$ in baboon plasma were measured using a capture ELISA. Microtiter plates (Costar, Cambridge, MA) were coated with 8.4 $\mu$g goat anti-mouse IgG, IgM, IgA (Organon Technika, Durham, N.C.) in 100 $\mu$l PBS buffer (Ortho Diagnostic Systems, Raritan, N.J.) overnight at 4° C. Goat anti-mouse antibody was removed and the plate blocked with 5% newborn calf serum (Irvine Scientific, Irvine, Calif.) in PBS for one hour at 37° C. Blocking solution was removed and 100 $\mu$l of test plasma or purified TF9-6B4 reference antibody, appropriately diluted in T-wash (50 mM tris (hydroxymethyl) aminomethane hydrochloride, 150 mM NaCl, 2.5% newborn calf serum, 2 mg/ml bovine serum albumin, 0.5% polyoxyethylene-sorbitan monolaurate 20, pH 7.6), was added to the microtiter wells. Microtiter plates were incubated one hour at 370° C. The test sample was removed and the plates were washed six times with PBS plus 0.5% polyoxyethylene-sorbitan monolaurate 20. One hundred microliters T-wash containing 250 $\mu$g horseradish peroxidase conjugated goat anti-mouse $IgG_1$ (Nordic Immunology, Tilburg, The Netherlands) was added to each well and incubated one hour at 37° C. Conjugated antibody was removed and the microtiter plate was washed six times with PBS plus 0.5% polyoxyethylenesorbitan monolaurate 20. O-phenylenediamine dihydrochloride substrate (Sigma, St. Louis, Mo.) was prepared according to the manufacturer's instructions and 100 $\mu$l was added to each well. Following a 30-minute incubation at room temperature, the reaction was stopped by addition of 50 $\mu$l/well 4N $H_2SO_4$ to each well. The $OD_{490}$ was read and the serum levels of murine IgG were calculated by comparison of $OD_{490}$ obtained from test samples with an $OD_{490}$ standard curve prepared from purified TF9-6B4.

Complete blood counts including leukocyte distribution, hematocrit, and platelet counts were performed on a System 9000 cell counter (Baker Instrument, Allentown, Pa.).

All data are presented as the mean or mean with standard derivation (SD). Analysis of the cohort data employed Student's t-test (one-tailed). Significance was set at p-0.05 for all determinations.

Baseline and post-MCA occlusion hematocrits, total leukocyte counts, platelet counts, and neurological scores between the TF9-6B4 treated group (n-6) and the untreated group (n-6) were not statistically different (Table 5). Both the anti-TF MoAb treated and the untreated groups displayed an abrupt, significant increase in total leukocyte count at the time of MCA occlusion. A non-significant rise in platelet count was seen in both the TF9-6B4 and untreated cohorts during ischemia and reperfusion.

TABLE 5

SERIAL HEMATOLOGIC STUDIES

| | N | Baseline | 60 min post-MCA Occlusion | 60 min post-Reperfusion⁺ |
|---|---|---|---|---|
| WBC (X $10^3/\mu l$) | 6 | 11.0 ± 2.1 | 21.8 ± 6.2 | 25.7 ± 3.6 |
| Untreated TF9-6B4 | 6 | 9.1 ± 2.9 | 27.1 ± 2.3 | 27.9 ± 3.2 |
| 2p | | 0.231 | 0.078 | 0.289 |
| Hematocrit (volume | 6 | 37.6 ± 4.7 | 38.5 ± 4.9 | 34.7 ± 3.8 |
| %) Untreated TF9-6B4 | 6 | 34.3 ± 1.3 | 34.2 ± 1.8 | 32.1 ± 4.2 |
| 2p | | 0.128 | 0.071 | 0.287 |
| Platelet (x $10^3/\mu l$) | 6 | 492 ± 27 | 540 ± 81 | 581 ± 102 |
| Untreated TF9-6B4 | 6 | 455 ± 136 | 555 ± 45 | 490 ± 42 |
| 2p | | 0.544 | 0.700 | 0.071 |

⁺Following 180 minutes MCA occlusion.

Figure 6:
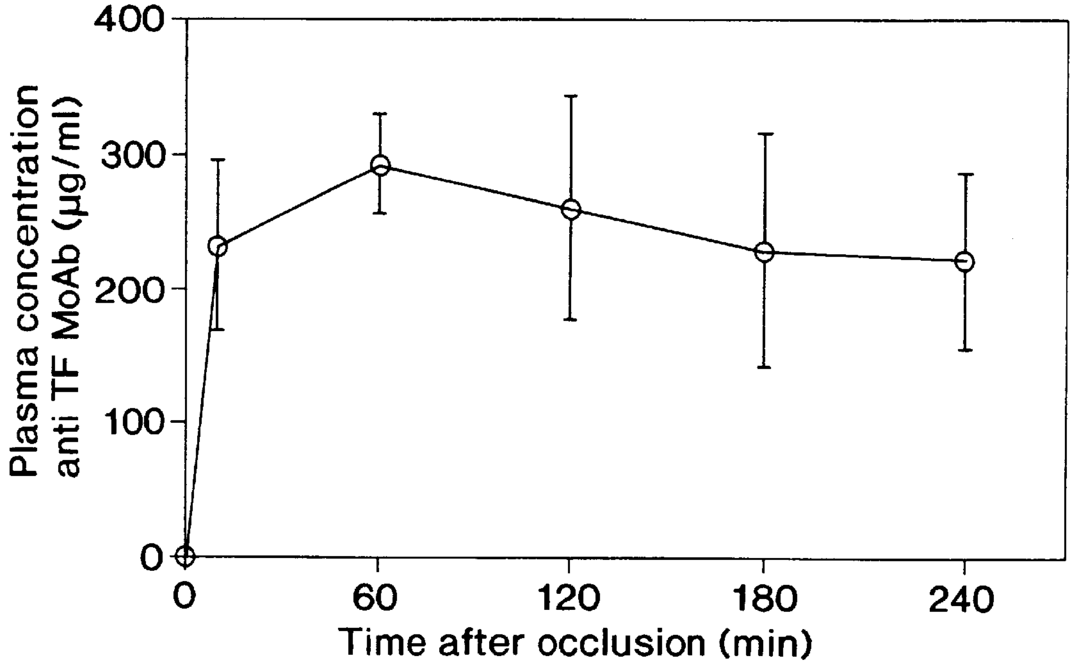
FIG. 6 shows the mean plasma concentrations of murine anti-TF MoAb following infusion MCA occlusion in a baboon model.

Plasma murine MaAb levels were significantly elevated over baseline within 10 minutes of infusion, reached a peak level within 1 hour, and remained significantly elevated throughout the ischemia/reperfusion period (FIG. 6). FIG. 6 shows the mean plasma concentrations of murine anti-TF MoAb following infusion MCA occlusion. All levels are significantly elevated compared to baseline (p<0.001).

Figure 7:
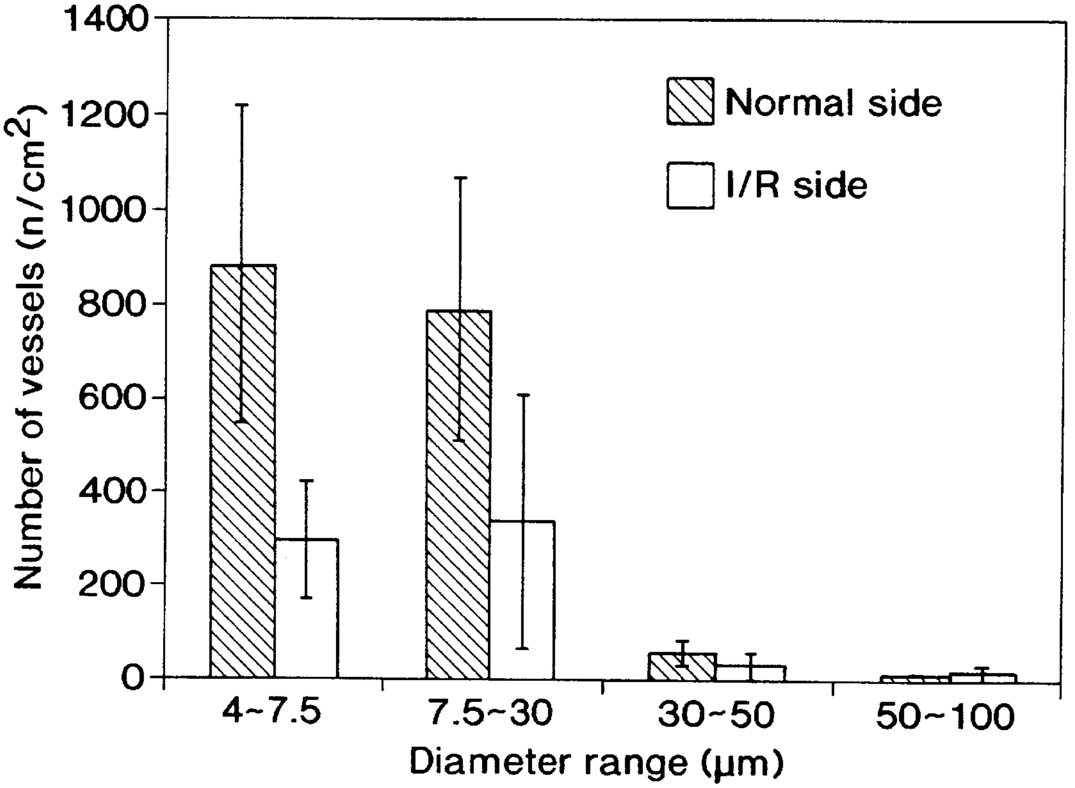
FIG. 7 shows the mean number of patent microvessels/$cm^2$ in non-ischemic and ischemia/reperfusion basal ganglia of untreated animals (baboon).

Following 180 minutes MCA occlusion and 60 minutes reperfusion of the LSA territory, the untreated group displayed a significant reduction in the number of patent microvessels of 4.0–7.5 $\mu$m (p-0.042) and 7.5–30.0 $\mu$m (p-0.009) minimum diameter in the ischemic basal ganglia compared to the non-ischemic basal ganglia (FIG. 7). FIG. 7 shows the mean number of patent microvessels/$cm^2$ in non-ischemic (cross-hatched) and ischemia/reperfusion (open) basal ganglia of untreated animals. A significant reduction in vessel patency is seen in the 4.0–7.5 $\mu$m (p-0.003) and 7.5–30 $\mu$m (p-0.018) diameter classes. These vessels are consistent with capillaries and with postcapillary venules/precapillary arteriole, respectively. The difference in the 30–50 $\mu$m and 50–100 $\mu$m diameter classes was not significant. The normalized patentcy difference ("percent reflow") in microvessels in the two size classes encompassing 50 to 100 $\mu$m diameter was not significant due to the small number of vessels contained in this size class and the variable percent reflow noted among subjects.

Figure 8:
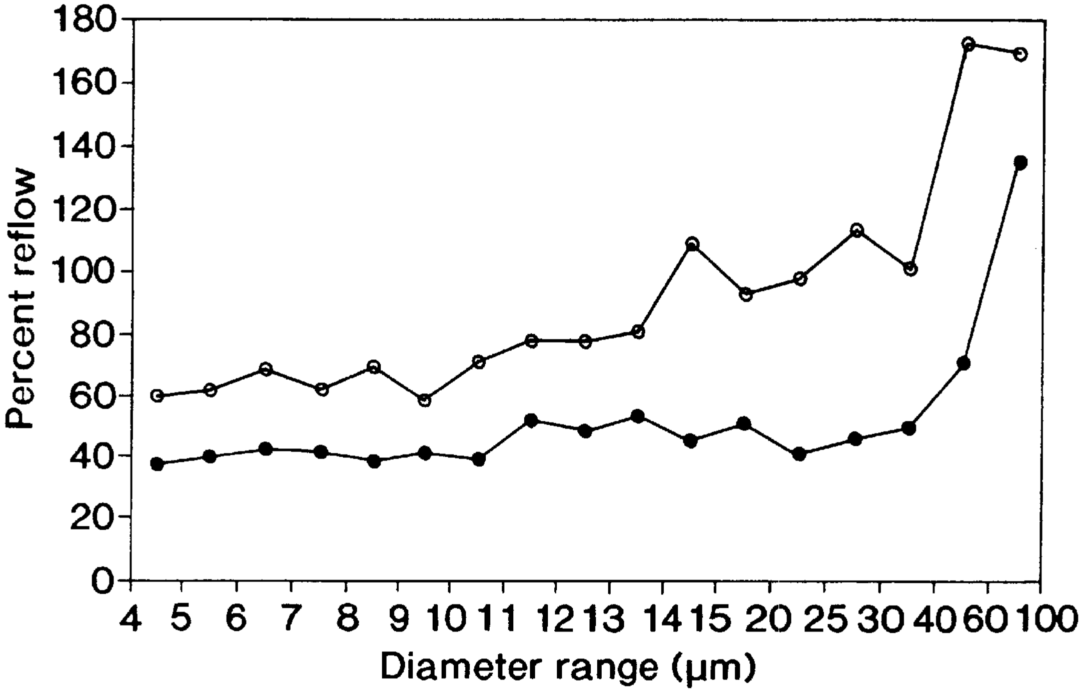
FIG. 8 shows the mean percent reflow by microvessel diameter in untreated and anti-TF MoAb treated subjects (baboon).
Figure 9:
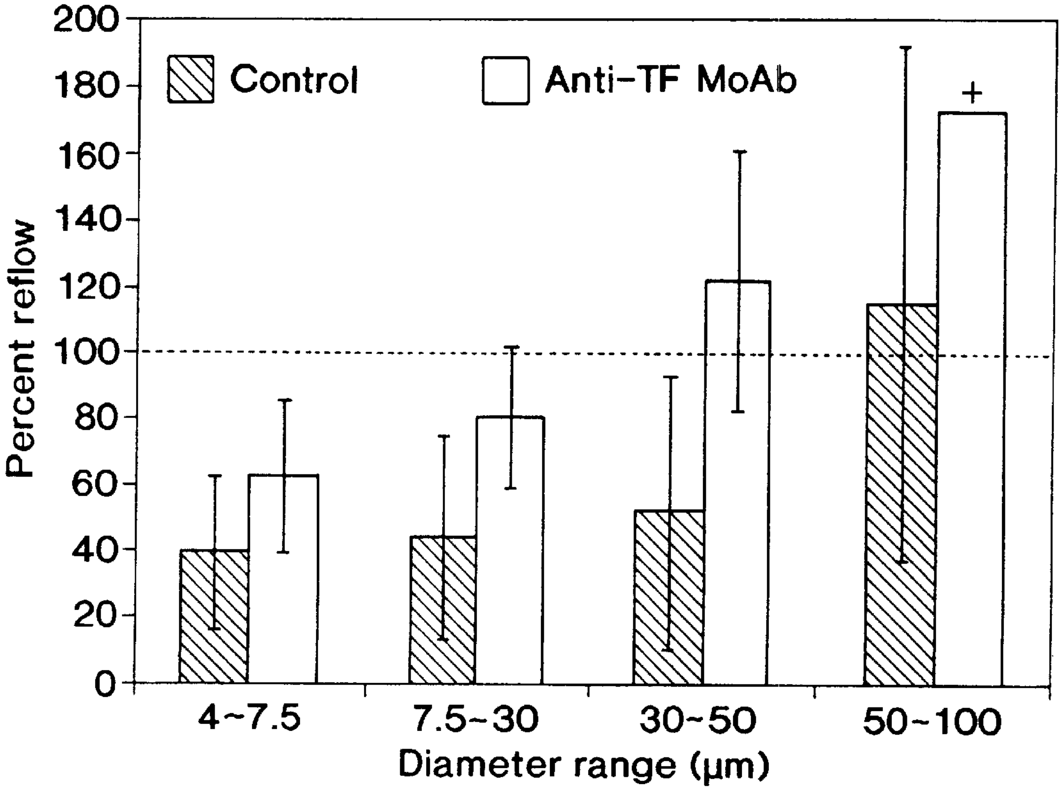
FIG. 9 shows the mean percent reflow in each diameter class of the untreated and anti-TF MoAb treated groups (baboon).

Infusion of the anti-TF MoAb just prior to MCA occlusion resulted in a significant increase in microvascular reflow (FIGS. 8 and 9). FIG. 8 shows the mean percent reflow by microvessel diameter in untreated (closed circles, n-6) and anti-TF MoAb treated (open circles, n-6) subjects. FIG. 9 shows the mean percent reflow in each diameter class of the untreated and anti-TF MoAb treated groups. The increase in the percent reflow in the 7.5–30 $\mu$m (p-0.038) and 30–50 $\mu$m (p-0.01 3) diameter classes was significant. Improved reflow in the 4.0–7.5 $\mu$m (p-0.1 18) and 50–100 $\mu$m (p-0.603) diameter classes did not reach significance. (+) S.D.=173.4. Improvement in reflow reached statistical significance in the microvessel classes of 7.5–30 $\mu$m diameter (postcapillary venules/precapillary arterioles) (p-0.038), and of 30–50 μm diameter (connecting venules/small arterioles) (p-0.01 3). An improvement in reflow following TF9-6B4 was seen in the capillary class of microvessels (4.0–7.5 μm diameter) which was not apparently significant (p-0.118).

Parenchymal hemorrhage was not a feature of the TF9-6B4 treated group. Hemorrhagic infarction seen in 4 of the 6 anti-TF MoAb exposed groups, was not different than 2 events seen in the untreated group.

Motor function measured by neurological assessment score declined within 5 to 15 minutes of MCA occlusion in all animals, and remained unchanged for the duration of each experiment (Table 6). The neurological score in animals treated with TF9-6B4 did not improve over the untreated group at any time during the ischemia and reperfusion period.

To evaluate any contribution of microvascular dilatation to the reflow improvement observed in the anti-TF MoAb group, the normalized proportion of microvessels in each size class was determined at 1 μm intervals. The means proportion of microvessels at each interval were nearly identical between the treated and untreated groups.

TABLE 6

| | | SERIAL NEUROLOGICAL SCORES MCA Occlusion (Ischemia)Reperfusion | | | | |
|---|---|---|---|---|---|---|
| | N | Baseline | 60 min | 120 min | 180 min | 60 min |
| Untreated | 6 | 100 | 60.7 ± 24.2 | 52.7 ± 15.3 | 57.0 ± 8.5 | 57.0 ± 18.5 |
| TF9-6B4 | 6 | 100 | 53.0 ± 14.1 | 52.1 ± 14.6 | 45.5 ± 22.2 | 45.5 ± 22.2 |
| 2p | | 0.178 | 0.581 | 0.640 | 0.310 | 0.460 |

Although the invention has been described with reference to the presently preferred embodiment, it should be understood that various modifications can be made without departing from the spirit of the invention. Accordingly, the invention is limited only by the following claims.

SUMMARY OF SEQUENCES

Sequence ID No. 1 is an amino acid sequence for a human TF binding site analog at amino acid residues 30–35 of the TF structural gene (page 14, line 16);

Sequence ID No. 2 is an amino acid sequence for a human TF binding site analog at amino acid residues 30–40 of the TF structural gene (page 14, line 20;

Sequence ID No. 3 is an amino acid sequence for a human TF binding site analog at amino acid residues 155–167 of the TF structural gene (page 14, line 21;

Sequence ID No. 4 is an amino acid sequence for a human TF binding site analog at amino acid residues 26–49 of the TF structural gene (page 14, line 26;

Sequence ID No. 5 is an amino acid sequence for a human TF binding site analog at amino acid residues 146–167 of the TF structural gene (page 14, line 27;

Sequence ID No. 6 is an amino acid sequence for a human TF binding site analog at amino acid residues 161–189 of the TF structural gene (page 15, Table 1, line 9;

Sequence ID No. 7 is an amino acid sequence for a human TF binding site analog at amino acid residues 1–30 of the TF structural gene (page 15, Table 1, line 10;

Sequence ID No. 8 is an amino acid sequence for a human TF binding site analog at amino acid residues 40–71 of the TF structural gene (page 15, Table 1, line 11;

Sequence ID No. 9 is an amino acid sequence for a human TF binding site analog at amino acid residues 41–49 of the TF structural gene (page 15, Table 1, line 12;

Sequence ID No. 10 is an amino acid sequence for a human TF binding site analog at amino acid residues 56–71 of the TF structural gene (page 15, Table 1, line 13;

Sequence ID No. 11 is an amino acid sequence for a human TF binding site analog at amino acid residues 72–104 of the TF structural gene (page 15, Table 1, line 14;

Sequence ID No. 12 is an amino acid sequence for a human TF binding site analog at amino acid residues 94–123 of the TF structural gene (page 15, Table 1, line 15;

Sequence ID No. 13 is an amino acid sequence for a human TF binding site analog at amino acid residues 190–209 of the TF structural gene (page 15, Table 1, line 16;

Sequence ID No. 14 is an amino acid sequence for a human TF binding site analog at amino acid residues 24–35 of the TF structural gene (page 15, Table 1, line 17);

Sequence ID No. 15 is an amino acid sequence for a human TF binding site analog at amino acid residues 144–159 of the TF structural gene (page 15, Table 1, line 18);

Sequence ID No. 16 is an amino acid sequence for a human TF binding site analog at amino acid residues 159–169 of the TF structural gene (page 15, Table 1, line 19);

Sequence ID No. 17 is an amino acid sequence for a human TF binding site analog at amino acid residues 157–169 of the TF structural gene (page 15, Table 1, line 20);

Sequence ID No. 18 is an amino acid sequence for a human TF binding site analog at amino acid residues 161–189 of the TF structural gene (page 15, Table 1, line 21);

Sequence ID No. 19 is a nucleotide sequence (and deduced amino acid sequence) of human tissue factor with the structural gene beginning at nucleotide 130 and ending at 918 (FIG. 1); and Sequence ID No. 20 is the deduced amino acid sequence of human tissue factor (FIG. 1).

I claim:

1. A method of inhibiting tissue factor (TF) mediated cerebral reperfusion tissue damage in a subject with cerebral ischemia or prior to or during a cerebral surgical procedure where blood flow in cerebral vessels is blocked off, by inhibiting blood coagulation which is initiated by binding of TF to a factor VII/VIIa complex, comprising:

administering to the subject a therapeutically effective amount of a monoclonal antibody produced by a hybridoma cell line selected from the group consisting of ATCC #HB9381, #HB9382, #HB9383, and monoclonal antibodies having all the identifying characteristics thereof, wherein the activity of TF is neutralized thereby inhibiting tissue damage.

2. The method of claim 1 wherein the monoclonal antibody has all the identifying characteristics of the monoclonal antibody produced by the hybridoma cell line ATCC # HB9381.

3. The method of claim 2, wherein the monoclonal antibody is produced by hybridoma cell line ATCC # HB9381.

4. The method of claim 1, wherein the subject is a mammal.

5. The method of claim 4, wherein the subject is a human.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single ( D ) TOPOLOGY: linear ( i i ) MOLECULE TYPE: peptide ( i x ) FEATURE:
( A ) NAME/KEY: Peptide
( B ) LOCATION: 1..6

( x i ) SEQUENCE DESCRIPTION: SEQ ID NO:1:

Val Asn Gln Val Tyr Thr
1 5

( 2 ) INFORMATION FOR SEQ ID NO:2:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..11

( x i ) SEQUENCE DESCRIPTION: SEQ ID NO:2:

Val Asn Gln Val Tyr Thr Val Gln Ile Ser Thr
1 5 10

( 2 ) INFORMATION FOR SEQ ID NO:3:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..13

( x i ) SEQUENCE DESCRIPTION: SEQ ID NO:3:

Leu Tyr Tyr Trp Lys Ser Ser Ser Ser Gly Lys Lys Thr
1 5 10

( 2 ) INFORMATION FOR SEQ ID NO:4:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..24

( x i ) SEQUENCE DESCRIPTION: SEQ ID NO:4:

Glu Pro Lys Pro Val Asn Gln Val Tyr Thr Val Gln Ile Ser Thr Lys
1 5 10 15

Ser Gly Asp Trp Lys Ser Lys Cys
20

( 2 ) INFORMATION FOR SEQ ID NO:5:

( i ) SEQUENCE CHARACTERISTICS:

(A) LENGTH: 22 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..22

(xi) SEQUENCE DESCRIPTION: SEQ ID NO:5:

```
Val Phe Gly Lys Asp Leu Ile Tyr Thr Leu Tyr Tyr Trp Lys Ser Ser
1               5                   10                  15

Ser Ser Gly Lys Lys Thr
            20
```

(2) INFORMATION FOR SEQ ID NO:6:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..29

(xi) SEQUENCE DESCRIPTION: SEQ ID NO:6:

```
Ser Ser Ser Gly Lys Lys Thr Ala Lys Thr Asn Thr Asn Glu Phe Leu
1               5                   10                  15

Ile Asp Val Asp Lys Gly Glu Asn Tyr Cys Phe Ser Val
            20                  25
```

(2) INFORMATION FOR SEQ ID NO:7:

(i) SEQUENCE CHARACTERISTICS:
(A) LENGTH: 30 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..30

(xi) SEQUENCE DESCRIPTION: SEQ ID NO:7:

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val
            20                  25                  30
```

(2) INFORMATION FOR SEQ ID NO:8:

(i) SEQUENCE CHARACTERISTICS:
(A) LENGTH: 32 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..32

-continued ( x i ) SEQUENCE DESCRIPTION: SEQ ID NO:8:

Thr Lys Ser Gly Asp Trp Lys Ser Lys Cys Phe Tyr Thr Thr Asp Thr
1 5 10 15

Glu Cys Asp Leu Thr Asp Glu Ile Val Lys Asp Val Lys Gln Thr Tyr
20 25 30

( 2 ) INFORMATION FOR SEQ ID NO:9:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..9

( x i ) SEQUENCE DESCRIPTION: SEQ ID NO:9:

Lys Ser Gly Asp Trp Lys Ser Lys Cys
1 5

( 2 ) INFORMATION FOR SEQ ID NO:10:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..16

( x i ) SEQUENCE DESCRIPTION: SEQ ID NO:10:

Glu Cys Asp Leu Thr Asp Glu Ile Val Lys Asp Val Lys Gln Thr Tyr
1 5 10 15

( 2 ) INFORMATION FOR SEQ ID NO:11:

( i ) SEQUENCE CHARACTERISTICS:
( A ) LENGTH: 34 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..34

( x i ) SEQUENCE DESCRIPTION: SEQ ID NO:11:

Leu Ala Arg Val Phe Ser Tyr Pro Ala Gly Asn Val Glu Ser Thr Gly
1 5 10 15

Ser Ala Gly Glu Pro Leu Tyr Glu Asn Ser Pro Glu Phe Thr Pro Tyr
20 25 30

Leu Cys ( 2 ) INFORMATION FOR SEQ ID NO:12:

( i ) SEQUENCE CHARACTERISTICS:
( A ) LENGTH: 30 amino acids
( B ) TYPE: amino acid
( C ) STRANDEDNESS: single -continued ( D ) TOPOLOGY: linear ( i i ) MOLECULE TYPE: peptide ( i x ) FEATURE:
( A ) NAME/KEY: Peptide
( B ) LOCATION: 1..30

( x i ) SEQUENCE DESCRIPTION: SEQ ID NO:12:

Tyr Glu Asn Ser Pro Glu Phe Thr Pro Tyr Leu Glu Thr Asn Leu Gly
1 5 10 15

Gln Pro Thr Ile Gln Ser Phe Glu Gln Val Gly Thr Lys Val
20 25 30

( 2 ) INFORMATION FOR SEQ ID NO:13:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..20

( x i ) SEQUENCE DESCRIPTION: SEQ ID NO:13:

Gln Ala Val Ile Pro Ser Arg Thr Val Asn Arg Lys Ser Thr Asp Ser
1 5 10 15

Pro Val Glu Cys
20

( 2 ) INFORMATION FOR SEQ ID NO:14:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..12

( x i ) SEQUENCE DESCRIPTION: SEQ ID NO:14:

Glu Trp Glu Pro Lys Pro Val Asn Gln Val Tyr Thr
1 5 10

( 2 ) INFORMATION FOR SEQ ID NO:15:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..16

( x i ) SEQUENCE DESCRIPTION: SEQ ID NO:15:

Arg Asp Val Phe Gly Lys Asp Leu Ile Tyr Thr Leu Tyr Tyr Trp Lys
1 5 10 15

-continued ( 2 ) INFORMATION FOR SEQ ID NO:16:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..13

( x i ) SEQUENCE DESCRIPTION: SEQ ID NO:16:

Tyr Trp Lys Ser Ser Ser Ser Gly Lys Lys Thr Ala Lys
1 5 10

( 2 ) INFORMATION FOR SEQ ID NO:17:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..13

( x i ) SEQUENCE DESCRIPTION: SEQ ID NO:17:

Tyr Trp Lys Ser Ser Ser Ser Gly Lys Lys Thr Ala Lys
1 5 10

( 2 ) INFORMATION FOR SEQ ID NO:18:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..29

( x i ) SEQUENCE DESCRIPTION: SEQ ID NO:18:

Ser Ser Ser Gly Lys Lys Thr Ala Lys Thr Asn Thr Asn Glu Phe Leu
1 5 10 15

Ile Asp Val Asp Lys Gly Glu Asn Tyr Cys Phe Ser Val
20 25

( 2 ) INFORMATION FOR SEQ ID NO:19:

( i ) SEQUENCE CHARACTERISTICS:
( A ) LENGTH: 1125 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 34..918
( D ) OTHER INFORMATION: /note= "nucleotide 130-918 is the structural gene for huTF"

( x i ) SEQUENCE DESCRIPTION: SEQ ID NO:19:

-continued

```
CGTTCCGCTC GATCTCGCCG CCAACTGGTA GAC ATG GAG ACC CCT GCC TGG CCC      54
                                     Met Glu Thr Pro Ala Trp Pro
                                      1               5

CGG GTC CCG CGC CCC GAG ACC GCC GTC GCT CGG ACG CTC CTG CTC GGC      102
Arg Val Pro Arg Pro Glu Thr Ala Val Ala Arg Thr Leu Leu Leu Gly
         10                  15                  20

TGG GTC TTC GCC CAG GTG GCC GGC GCT TCA GGC ACT ACA AAT ACT GTG      150
Trp Val Phe Ala Gln Val Ala Gly Ala Ser Gly Thr Thr Asn Thr Val
     25                  30                  35

GCA GCA TAT AAT TTA ACT TGG AAA TCA ACT AAT TTC AAG ACA ATT TTG      198
Ala Ala Tyr Asn Leu Thr Trp Lys Ser Thr Asn Phe Lys Thr Ile Leu
 40                  45                  50                  55

GAG TGG GAA CCC AAA CCC GTC AAT CAA GTC TAC ACT GTT CAA ATA AGC      246
Glu Trp Glu Pro Lys Pro Val Asn Gln Val Tyr Thr Val Gln Ile Ser
                 60                  65                  70

ACT AAG TCA GGA GAT TGG AAA AGC AAA TGC TTT TAC ACA ACA GAC ACA      294
Thr Lys Ser Gly Asp Trp Lys Ser Lys Cys Phe Tyr Thr Thr Asp Thr
             75                  80                  85

GAG TGT GAC CTC ACC GAC GAG ATT GTG AAG GAT GTG AAG CAG ACG TAC      342
Glu Cys Asp Leu Thr Asp Glu Ile Val Lys Asp Val Lys Gln Thr Tyr
         90                  95                 100

TTG GCA CGG GTC TTC TCC TAC CCG GCA GGG AAT GTG GAG AGC ACC GGT      390
Leu Ala Arg Val Phe Ser Tyr Pro Ala Gly Asn Val Glu Ser Thr Gly
    105                 110                 115

TCT GCT GGG GAG CCT CTG TAT GAG AAC TCC CCA GAG TTC ACA CCT TAC      438
Ser Ala Gly Glu Pro Leu Tyr Glu Asn Ser Pro Glu Phe Thr Pro Tyr
120                 125                 130                 135

CTG GAG ACA AAC CTC GGA CAG CCA ACA ATT CAG AGT TTT GAA CAG GTG      486
Leu Glu Thr Asn Leu Gly Gln Pro Thr Ile Gln Ser Phe Glu Gln Val
                140                 145                 150

GGA ACA AAA GTG AAT GTG ACC GTA GAA GAT GAA CGG ACT TTA GTC AGA      534
Gly Thr Lys Val Asn Val Thr Val Glu Asp Glu Arg Thr Leu Val Arg
            155                 160                 165

AGG AAC AAC ACT TTC CTA AGC CTC CGG GAT GTT TTT GGC AAG GAC TTA      582
Arg Asn Asn Thr Phe Leu Ser Leu Arg Asp Val Phe Gly Lys Asp Leu
        170                 175                 180

ATT TAT ACA CTT TAT TAT TGG AAA TCT TCA AGT TCA GGA AAG AAA ACA      630
Ile Tyr Thr Leu Tyr Tyr Trp Lys Ser Ser Ser Ser Gly Lys Lys Thr
    185                 190                 195

GCC AAA ACA AAC ACT AAT GAG TTT TTG ATT GAT GTG GAT AAA GGA GAA      678
Ala Lys Thr Asn Thr Asn Glu Phe Leu Ile Asp Val Asp Lys Gly Glu
200                 205                 210                 215

AAC TAC TGT TTC AGT GTT CAA GCA GTG ATT CCC TCC CGA ACA GTT AAC      726
Asn Tyr Cys Phe Ser Val Gln Ala Val Ile Pro Ser Arg Thr Val Asn
                220                 225                 230

CGG AAG AGT ACA GAC AGC CCG GTA GAG TGT ATG GGC CAG GAG AAA GGG      774
Arg Lys Ser Thr Asp Ser Pro Val Glu Cys Met Gly Gln Glu Lys Gly
            235                 240                 245

GAA TTC AGA GAA ATA TTC TAC ATC ATT GGA GCT GTG GTA TTT GTG GTC      822
Glu Phe Arg Glu Ile Phe Tyr Ile Ile Gly Ala Val Val Phe Val Val
        250                 255                 260

ATC ATC CTT GTC ATC ATC CTG GCT ATA TCT CTA CAC AAG TGT AGA AAG      870
Ile Ile Leu Val Ile Ile Leu Ala Ile Ser Leu His Lys Cys Arg Lys
    265                 270                 275

GCA GGA GTG GGG CAG AGC TGG AAG GAG AAC TCC CCA CTG AAT GTT TCA      918
Ala Gly Val Gly Gln Ser Trp Lys Glu Asn Ser Pro Leu Asn Val Ser
280                 285                 290                 295

TAAAGGAAGC ACTGTTGGAG CTACTGCAAA TGCTATATTG CACTGTGACC GAGAACTTTT    978

AAGAGTGCCC TAGGACAGAA CCTGTGCCAG AAAGGAAAGT AAAGGAACAG TGCGAGTGGA   1038
```

AGTCCAGAGG CAAGAAGGAA CATGGCAGGA TGCAGGTACA GGAGGGTGCA TAGCCTGGCC 1098

TGAGTGCTGT GTTCTGGAAA GGAGTGG 1125

( 2 ) INFORMATION FOR SEQ ID NO:20:

( i ) SEQUENCE CHARACTERISTICS:
( A ) LENGTH: 295 amino acids
( B ) TYPE: amino acid
( D ) TOPOLOGY: linear ( i i ) MOLECULE TYPE: protein ( x i ) SEQUENCE DESCRIPTION: SEQ ID NO:20:

Met Glu Thr Pro Ala Trp Pro Arg Val Pro Arg Pro Glu Thr Ala Val
1 5 10 15

Ala Arg Thr Leu Leu Leu Gly Trp Val Phe Ala Gln Val Ala Gly Ala
20 25 30

Ser Gly Thr Thr Asn Thr Val Ala Ala Tyr Asn Leu Thr Trp Lys Ser
35 40 45

Thr Asn Phe Lys Thr Ile Leu Glu Trp Glu Pro Lys Pro Val Asn Gln
50 55 60

Val Tyr Thr Val Gln Ile Ser Thr Lys Ser Gly Asp Trp Lys Ser Lys
65 70 75 80

Cys Phe Tyr Thr Thr Asp Thr Glu Cys Asp Leu Thr Asp Glu Ile Val
85 90 95

Lys Asp Val Lys Gln Thr Tyr Leu Ala Arg Val Phe Ser Tyr Pro Ala
100 105 110

Gly Asn Val Glu Ser Thr Gly Ser Ala Gly Glu Pro Leu Tyr Glu Asn
115 120 125

Ser Pro Glu Phe Thr Pro Tyr Leu Glu Thr Asn Leu Gly Gln Pro Thr
130 135 140

Ile Gln Ser Phe Glu Gln Val Gly Thr Lys Val Asn Val Thr Val Glu
145 150 155 160

Asp Glu Arg Thr Leu Val Arg Arg Asn Asn Thr Phe Leu Ser Leu Arg
165 170 175

Asp Val Phe Gly Lys Asp Leu Ile Tyr Thr Leu Tyr Tyr Trp Lys Ser
180 185 190

Ser Ser Ser Gly Lys Lys Thr Ala Lys Thr Asn Thr Asn Glu Phe Leu
195 200 205

Ile Asp Val Asp Lys Gly Glu Asn Tyr Cys Phe Ser Val Gln Ala Val
210 215 220

Ile Pro Ser Arg Thr Val Asn Arg Lys Ser Thr Asp Ser Pro Val Glu
225 230 235 240

Cys Met Gly Gln Glu Lys Gly Glu Phe Arg Glu Ile Phe Tyr Ile Ile
245 250 255

Gly Ala Val Val Phe Val Val Ile Ile Leu Val Ile Ile Leu Ala Ile
260 265 270

Ser Leu His Lys Cys Arg Lys Ala Gly Val Gly Gln Ser Trp Lys Glu
275 280 285

Asn Ser Pro Leu Asn Val Ser
290 295